United States Patent [19]

Fukuda

[11] Patent Number: 5,320,943
[45] Date of Patent: Jun. 14, 1994

[54] METHODS OF DETECTING T-CELL DYSFUNCTIONS

[75] Inventor: Minoru Fukuda, San Diego, Calif.

[73] Assignee: La Jolla Cancer Research Foundation, La Jolla, Calif.

[21] Appl. No.: 677,099

[22] Filed: Mar. 29, 1991

[51] Int. Cl.$^5$ .................. G01N 33/53; G01N 33/544; C07K 15/00; C12Q 1/48

[52] U.S. Cl. ..................................... 435/7.24; 435/15; 435/7.23; 435/7.4; 530/395; 436/64

[58] Field of Search ............... 435/7.24, 15, 74; 530/395; 436/64

[56] References Cited

U.S. PATENT DOCUMENTS 4,366,242  12/1982  Neumann et al. ................. 435/7.4

OTHER PUBLICATIONS

Dunphy, W. G. et al., Cell 40:463–72, 1985.
Reisinger et al., "Molecular Heterogeneity of a Lymphocyte Glycoprotein in Immunodeficient Patients", J. Clin. Invest., 79:595, 1987.
Borche et al., "CD43 monoclonal antibodies recognize the large sialoglycoprotein of human leukocytes", Eur. J. Immunol., 17:1523, 1987.
Greer et al., "Altered Expression of leucocyte sialoglycoprotein in Wiskott–Aldrich syndrome is associated with a specific defect in O-glycoylation", Biochem. Cell Biol., 67:503–509, 1989.
S. Carlsson et al., Structural Variations of O-Linked Oligosaccharides Present in Leukosialin Isolated from Erythroid, Myeloid, and T–Lymphoid Cell Lines, The Journal of Biological Chemistry, 261:12787–12791 (1986).
Fukuda et al., Structures of O-Linked Oligosaccharides Isolated from Normal Granulocytes, Chronic Myelogenous Leukemia Cells, and Acute Myelogenous Leukemia Cells, The Journal of Biological Chemistry, 261:12796–12806 (1986).
Carl G. Gahmberg and Leif C. Anderson, Identification and Characterization of Normal and Malignant Human Blood Leukocytes by Surface Glycoprotein Patterns, Annals New York Academy of Sciences, 240–255 (1978).
Minoru Fukuda, Cell Surface Glycoconjugates as Onco-Differentiation Markers in Hematopoietic Cells, Biochimica et Biophysica Acta 780:119–150 (1985).
Minoru Fukuda, Leukosialin, a major sialoglycoprotein defining leucocyte differentiation, Carbohydrate recognition in cellular function. Wiley, Chichester (Ciba Foundation Symposium 145) 257–276 (1989).
F. Piller et al., Human T-lymphocyte Activation is Associated with Changes in O-Glycan Biosynthesis, The Journal of Biological Chemistry 263:15146–15150 (1988).
E. A. Higgins et al., Defective O-Linked Glycosylation in Lymphocytes From Patients with the Wiskott–Aldrich Syndrome, Glycoconj. J., 2:478 (1990).
F. Piller et al., Resting Lymphocytes in Wiskott–Aldrich–Syndrome Carry O-Glycans Specific for Activated Normal T–cell, J. Cell Biol., 108:191a (1989).

*Primary Examiner*—Esther L. Kepplinger
*Assistant Examiner*—Nancy J. Parsons
*Attorney, Agent, or Firm*—Campbell and Flores

[57] ABSTRACT

A method is provided for detecting T-cell dysfunctions. The method includes detecting an alteration in the level of a protein regulating synthesis of the hexasaccharide NeuNAc$\alpha$2→3Gal$\beta$1→3(NeuNAc$\alpha$2→3Gal$\beta$1→4GlcNAc$\beta$1→6)GalNAc on leukosialin of T-cells from a subject suspected of having a T-cell dysfunction compared to resting T-cells from a normal individual. The protein regulating synthesis of the hexasaccharide can be core 2 GlcNAc transferase and can be detected by either a change in its amount or activity. Also provided is a method of detecting T-cell dysfunctions which includes detecting an alteration in the level of leukosialin having the hexasaccharide NeuNAc$\alpha$2→3Gal$\beta$1→3(NeuNAc$\alpha$2→3Gal$\beta$1→4GlcNAc$\beta$1→6)GlcNAc on T-cells from a subject suspected of having a T-cell dysfunction compared to resting T-cells from a normal individual. Kits for detecting T-cell dysfunction are provided as well.

15 Claims, 17 Drawing Sheets

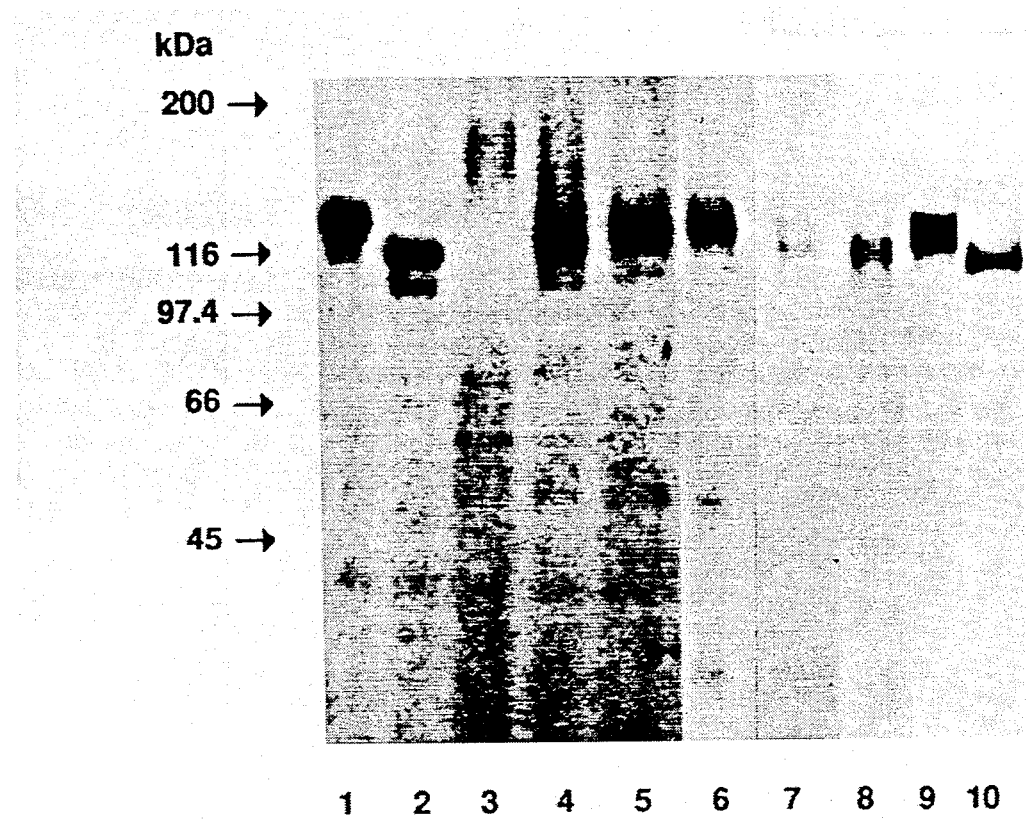
FIG. IA
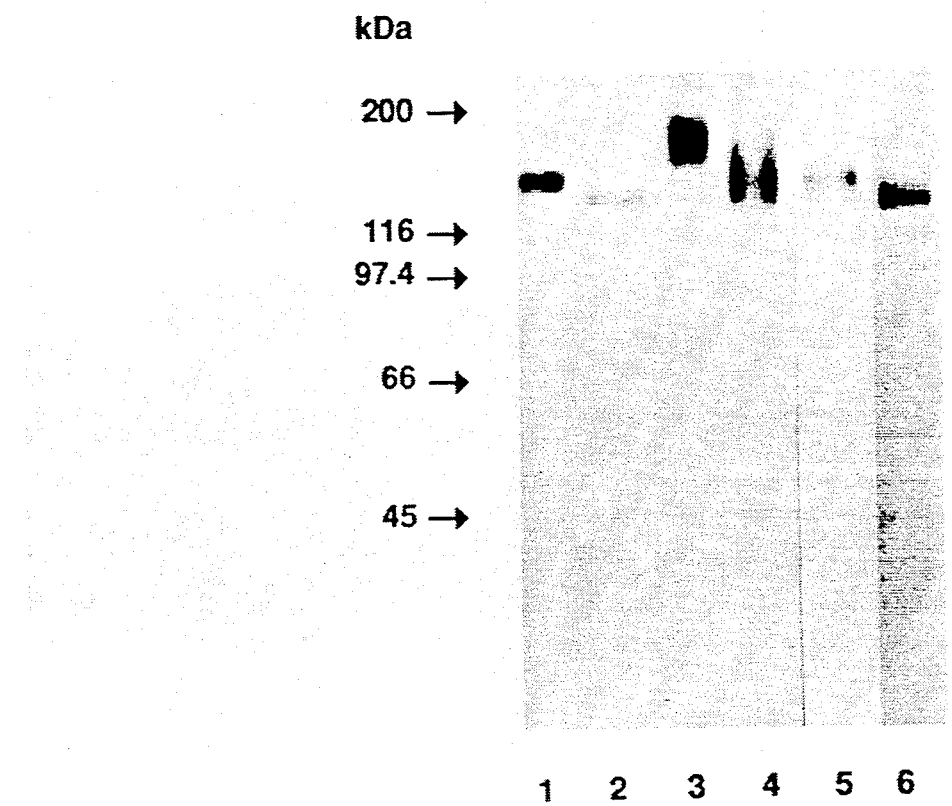
FIG. IB

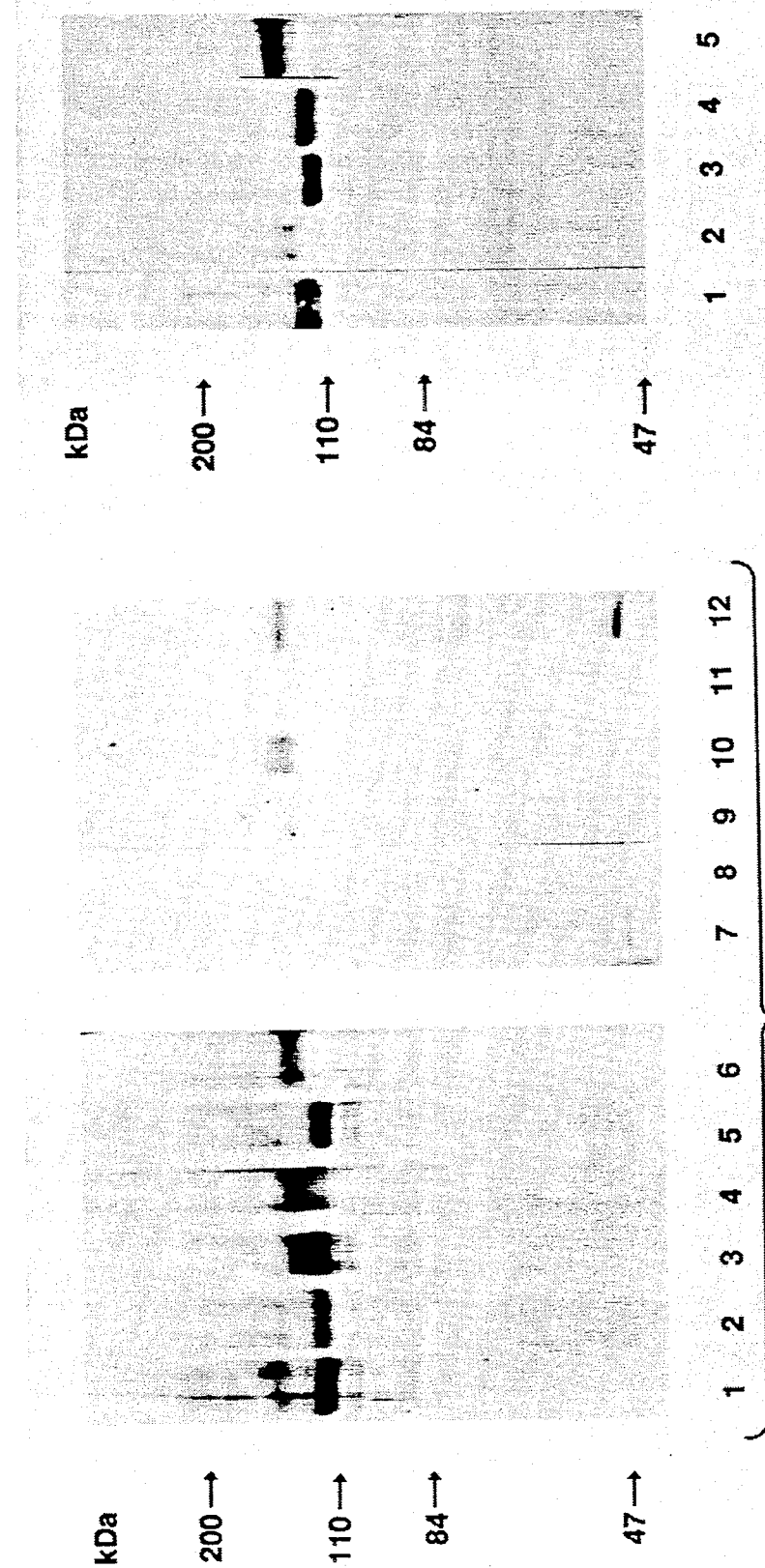

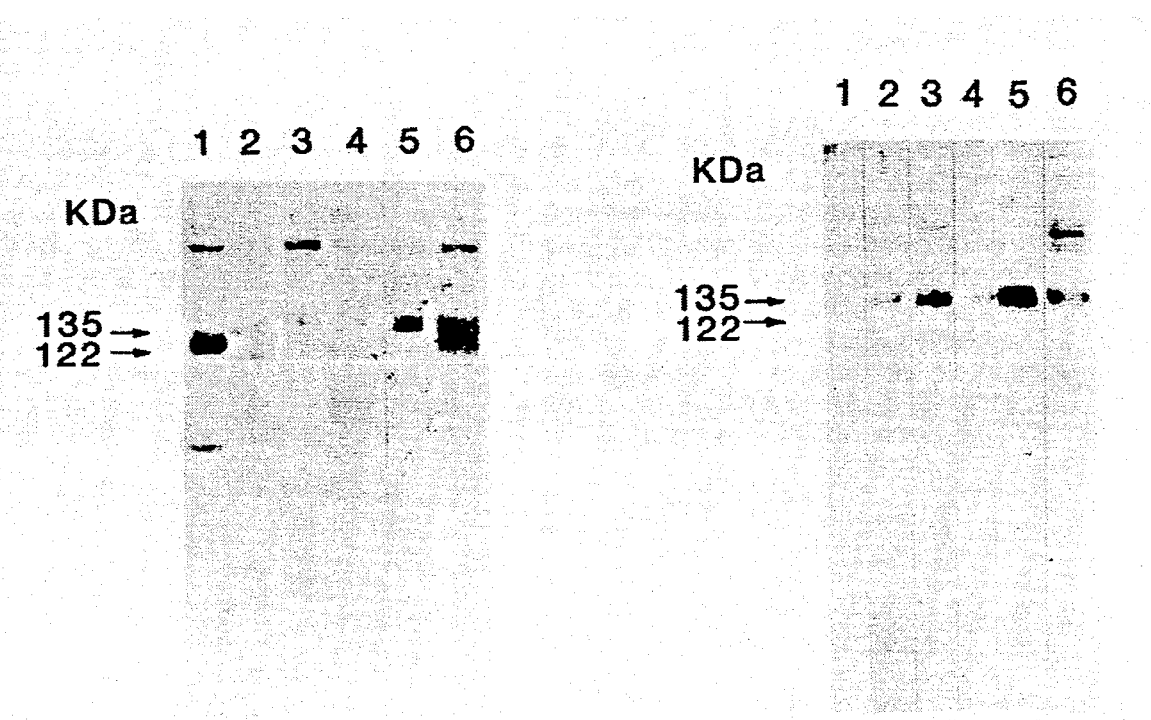
FIG. 9A
FIG. 9B
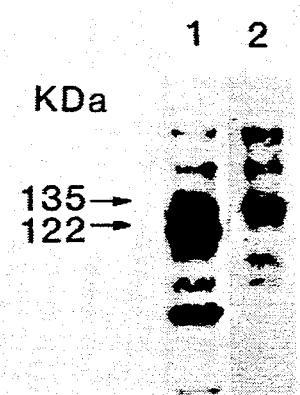
FIG. 9C

METHODS OF DETECTING T-CELL DYSFUNCTIONS

BACKGROUND OF THE INVENTION

The present invention was made with support of National Cancer Institute grant number CA 33895. The United States Government may have rights in the invention.

The invention relates generally to cell surface carbohydrate markers, and more specifically to a method of detecting T-cell dysfunctions using a specific hexasaccharide structure found on the protein leukosialin.

The hematopoietic system can be divided into two major cell lineages. The first consists of the myeloid cell lineage and is responsible for functions such as oxygen exchange, destruction of invading bacteria, modulation of allergic inflammatory reactions and blood clotting. Cells of the myeloid lineage which mediate these functions include erythrocytes, granulocytes, monocytes, eosinophils and platelets.

The second major lineage within the hematopoietic system consists of the lymphoid cell lineage. This class is primarily responsible for host immunity and includes B-lymphocytes (B-cells) and T-lymphocytes (T-cells). B-cells are responsible for antibody-mediated immunity. Antibodies produced by B-cells circulate in the blood stream and are capable of binding and neutralizing a foreign antigen. T-cells, on the other hand, function in cell-mediated immunity. They are involved in a wide variety of immune functions, all of which involve the direct interaction of the T-cell with some other cell. The interacting cell can be another T-lymphocyte, a B-lymphocyte, a macrophage or a target cell. In the latter case, the antigen to be recognized is generally found at the surface of a target cell. Types of T-lymphocytes include, for example, helper T-cells, suppressor T-cells and cytotoxic T-cells.

The ability of the immune system to perform both antibody-mediated and cell-mediated immunity is the basis of our defense against invading pathogenic organisms. These two types of immune response can be dissociated to a large extent but not without compromising the host's ability to provide complete protection. For instance, in humans, congenital agammaglobulinemia is a disease in which antibody-mediated immunity is deficient while cell-mediated immunity is normal. In contrast, congenital thymus deficiencies produce individuals with greatly impaired cell-mediated immunity but relatively high serum antibody levels.

In many instances, an individual cannot survive without the function of both immunities. For example, loss of T-cell function due to cancers such as acute T-lymphocytic leukemia (T-ALL) can eventually lead to death. In this disease, the normal population of T-cells is overtaken by the faster growing malignant population until complete loss of normal T-cell-mediated immunity occurs. Acquired Immune Deficiency Syndrome (AIDS) is another disease where complete loss of T-cell function results in death. AIDS is caused by infection with a retrovirus. An analogous example of a congenital T-cell immunodeficiency is Wiscott-Aldrich Syndrome (WAS).

Cell surface carbohydrate structures have been used as tumor or differentiation markers since they are known to undergo characteristic changes during differentiation. For example, leukemic cells have been classified by their surface glycoprotein molecular weight patterns with respect to their relationship to normal blood cells (Gahmberg and Andersson, Annals New York Academy of Sciences 240–255 (1978). For a detailed review of such onco-differentiation markers as they apply to the myeloid cell lineage, see Fukuda, Biochimica et Biophysica Acta 780:119–150 (1985), which is incorporated herein by reference.

One of the most extensively studied markers is a major sialoglycoprotein known as leukosialin, also known as sialophorin or CD43. It is an integral membrane protein which carries one N-linked and eighty O-linked carbohydrate chains. Its mobility on SDS-PAGE depends largely on the structures of the O-linked glycans and the extent of sialiation. This glycoprotein has been shown to be differentially glycosylated between different leukemic cell lines and to increase in molecular weight upon activation of normal human T-cells, Carlsson et al., The Journal of Biological Chemistry 261:12787–12791 (1986), and Piller et al., The Journal of Biological Chemistry 263:15146–15150 (1988). The differential glycosylation between leukemic cell lines is due to characteristic sets of O-linked oligosaccharides whereas the increase in molecular weight upon activation is due exclusively to the expression of a branched hexasaccharide structure. Resting T-cells express on leukosialin the tetrasaccharide NeuNAc$\alpha$2→3Gal$\beta$1→3(NeuNAc$\alpha$2→6)GalNAc-Ser/Thr but activated T-cells carry the more complex structure NeuNAc$\alpha$2→3Gal$\beta$1→3(NeuNAc$\alpha$2→3Gal$\beta$1→4GlcNAc$\beta$1→6)GalNAc-Ser/Thr. This branched hexasaccharide structure has also been found on leukosialin from T-lymphocytes isolated from WAS patients, Piller et al., J. Cell Biol. 108:191a (1989), and on cell surface glycoproteins of the myeloid cell lineage, Fukuda et al., The Journal of Biological Chemistry 261:12796–12806 (1986), both of which are incorporated herein by reference.

The shift in biosynthesis of O-glycans in activated T-cells compared to resting T-cells is apparently caused by a stimulation of the $\beta$1→6GlcNAc-transferase (Core 2 GlcNAc-T). Activated T-cells also exhibit a concomitant decrease in $\alpha$2→6 sialyltransferase activity. This shift in glycosyltransferase activity results in a decrease in the amount of tetrasaccharide expressed on leukosialin paralleled by an increase in the amount of expressed hexasaccharide, Piller et al., (1988) supra.

Despite the increased interest in the elucidation of cell surface structures and their biosynthetic mechanisms, very few markers have been discovered which accurately predict pathological disorders of cell-mediated immunity. Leukosialin has been extensively characterized as a marker for normal T-cell activation. However, there has been no indication that this determinant can also be used as a marker for pathologic T-cell dysfunctions.

There thus exists a need for a method which can accurately diagnose T-cell dysfunctions. The present invention satisfies this need and provides related advantages as well.

SUMMARY OF THE INVENTION

A method is provided for detecting T-cell dysfunctions. The method includes detecting an alteration in the level of a protein regulating synthesis of the hexasaccharide NeuNAc$\alpha$2→3Gal$\beta$1→3(NeuNAc$\alpha$2→3Gal$\beta$1→4GlcNAc$\beta$1→6)GalNAc on leukosialin of T-cells from a subject suspected of having a T-cell dysfunction compared to resting T-cells from a normal individual. The protein regulating synthesis of the hexasaccharide can be core 2 GlcNAc transferase and can be detected by either a change in its amount or activity. Also provided is a method of detecting T-cell dysfunctions which includes detecting an alteration in the level of leukosialin having the hexasaccharide NeuNAcα2→3Galβ1→3(NeuNAcα2→3Galβ1→4 GlcNAcβ1→6)GlcNAc on T-cells from a subject suspected of having a T-cell dysfunction compared to resting T-cells from a normal individual. Kits for detecting T-cell dysfunction are provided as well.

BRIEF DESCRIPTION OF THE DRAWINGS

FIGS. 1 and 1B show leukosialin immunoprecipitated from various cells after cell surface labeling by periodate oxidation followed by NaB[$^3$H]$_4$ reduction or by galactose oxidase/NaB[$^3$H]$_4$ procedure after sialidase treatment. Immunoprecipitates were analyzed by SDS-polyacrylamide gel electrophoresis followed by fluorography, as described in Example I. FIG. 1A, Leukosialin labeled at sialic acid residues from HSB-2 (lane 1), K562 (lane 2), HL-60 (lane 3), three different T-ALL (lanes 4–6), two different T-CLL (lanes 7 and 8) or thymocytes (lane 9) or peripheral lymphocytes of a normal individual (lane 10). FIG. 1B, Leukosialin, labeled at galactose and N-acetylgalactosamine residues after removal of sialic acid, from HSB-2 (lane 1), K562 (lane 2), HL-60 (lane 3), T-CLL (lane 4), T-ALL (lane 5), and peripheral lymphocytes of a normal individual (lane 6).

FIGS. 3A and 3C, glycopeptides prepared from leukosialin of T-ALL (3A) or T-CLL (3C). FIGS. 3B and 3D, oligosaccharides released by alkaline borohydride treatment from the glycopeptides pooled from 3A (3B) or 3C (3D). Sephadex G-50 gel filtration was carried out as described in Example II. Fractions were pooled as indicated by bars.

1. NeuNAcα2→3Galβ1→3(NeuNAcα2→3Galβ1→4GlcNAcβ1→6)GalNaCOH,
2. NeuNAcα2→3Galβ1→3(NeuNAcα2→6)GalNAcOH,
3. NeuNAcα2→3Galβ1→4GlcNAcβ1→6-(Galβ1→3)GalNAcOH and NeuNAcα2→3Galβ1→3(Galβ1→4GlcNAcβ1→6)GalNAcOH,
4. NeuNAcα2→3Galβ1→3GalNAcOH.

O-linked oligosaccharides from T-CLL (4A), T-ALL (4B), normal peripheral T-lymphocytes (4C) and thymocytes (4D) were applied to the column under the same conditions described in Example II.

Figure 4A:
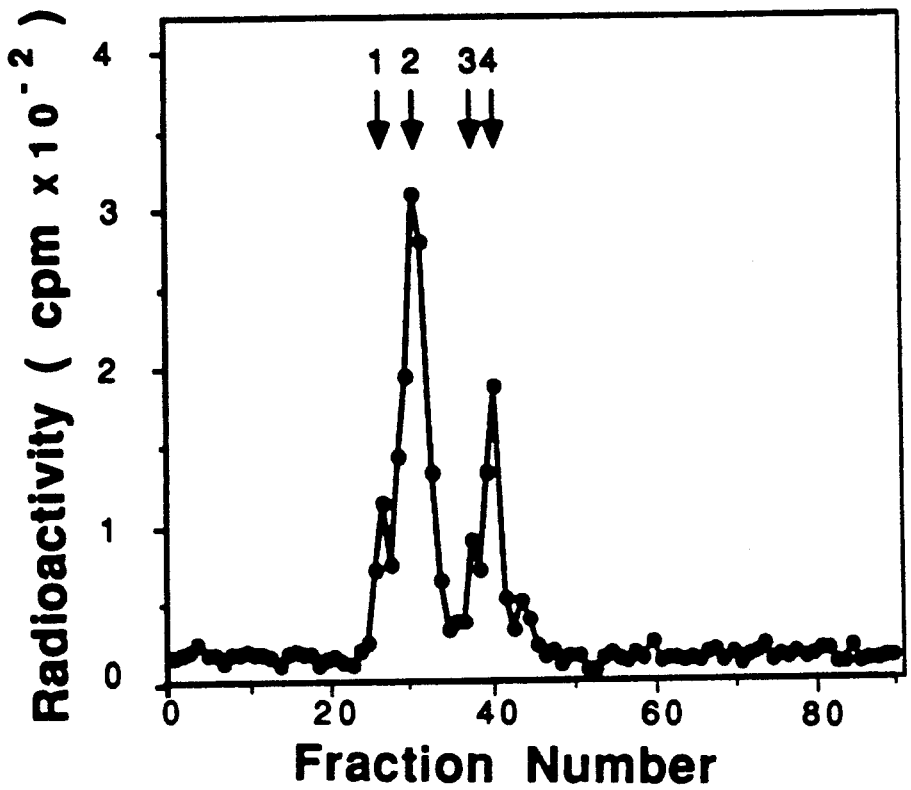
FIGS. 4A–4D show Bio-Gel P-4 gel filtration of O-linked oligosaccharides from T-CLL, T-ALL, normal resting T-lymphocytes, and thymocytes. O-linked oligosaccharides were isolated by Sephadex G-50 gel filtration as shown in FIGS. 3B and 3D and subjected to Bio-Gel P-4 gel filtration. The elution positions of standard oligosaccharides are indicated by arrows.
Figure 4B:
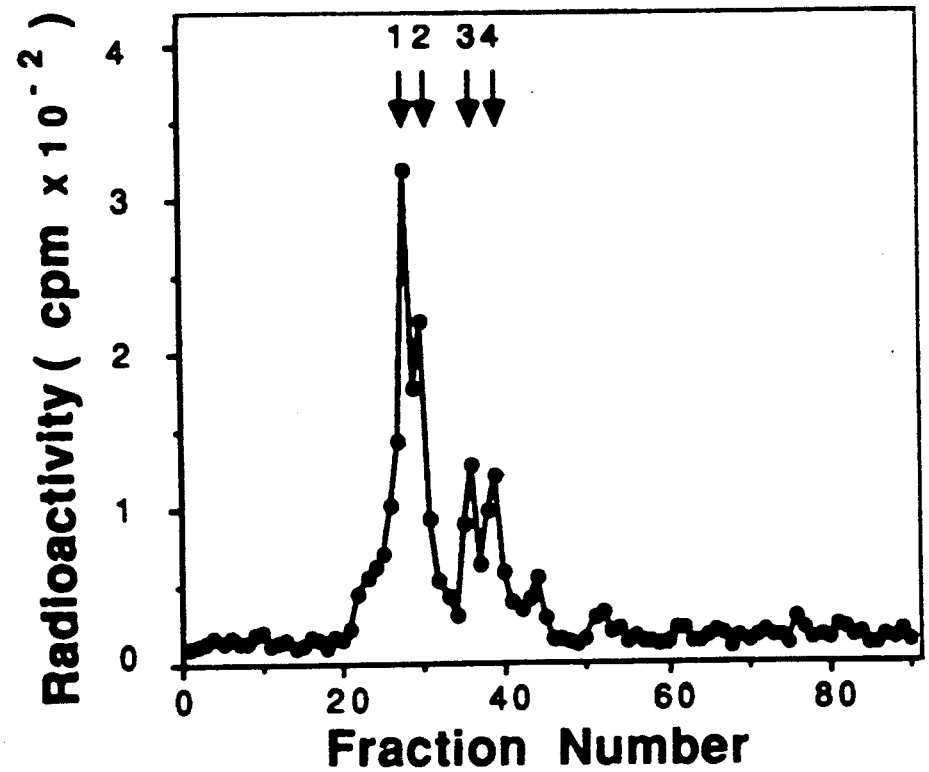
Figure 4C:
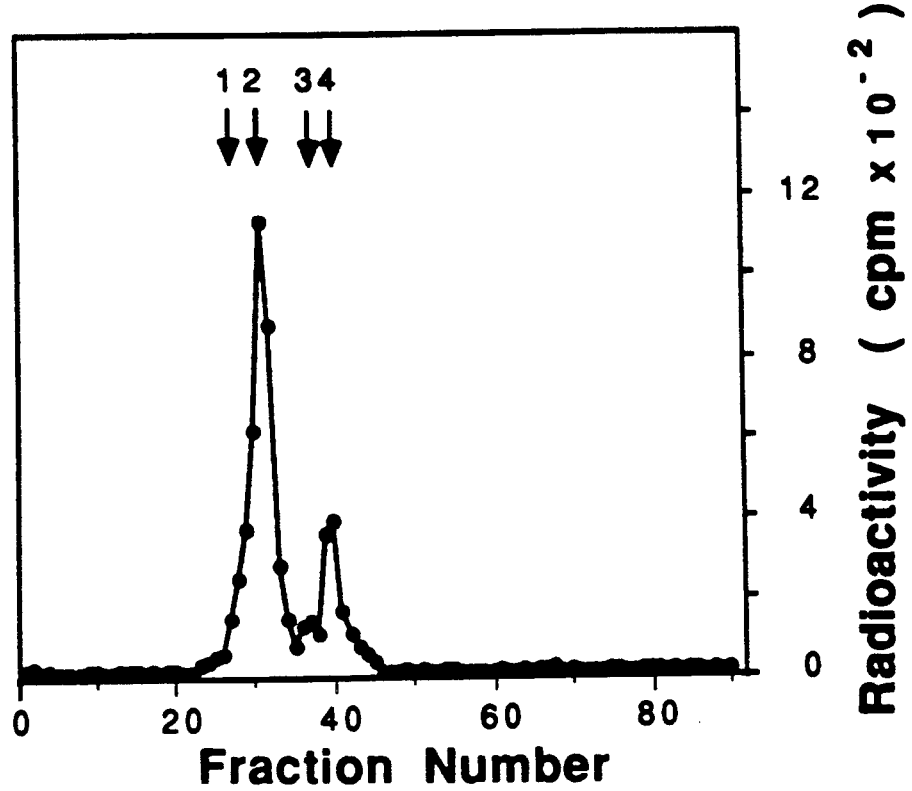
Figure 4D:
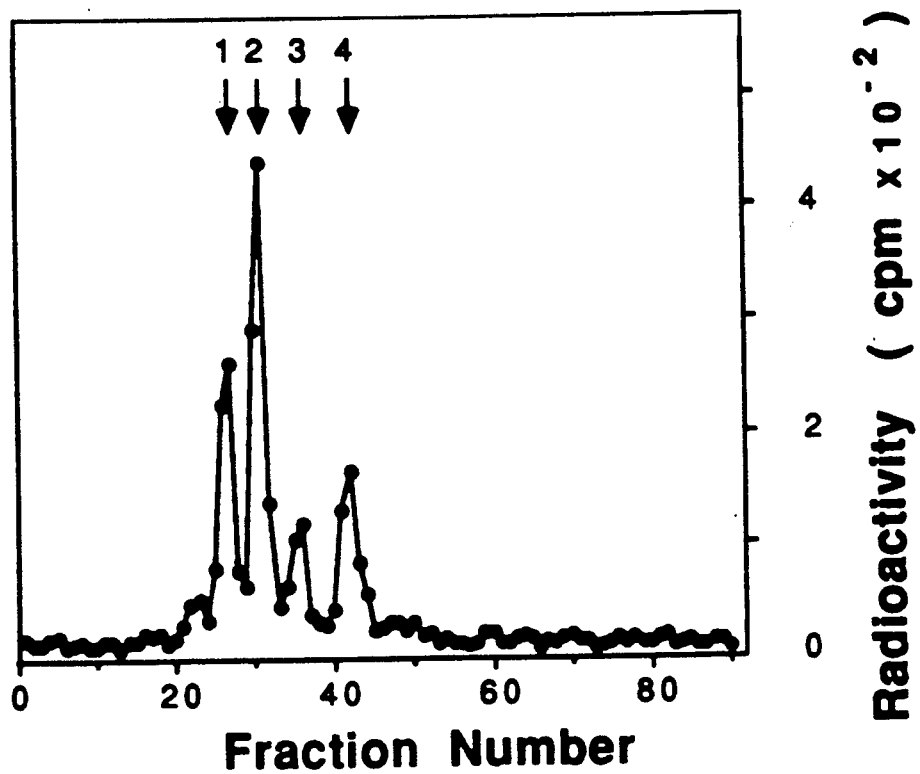
Figure 5A:
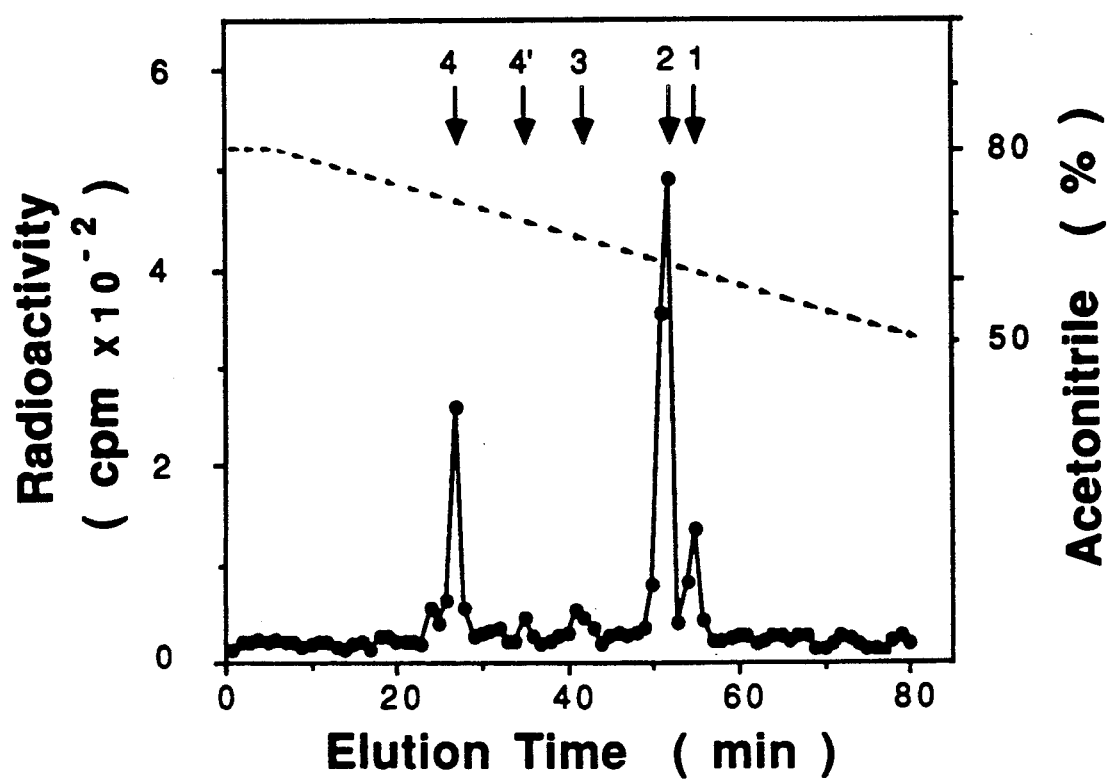
Figure 5B:
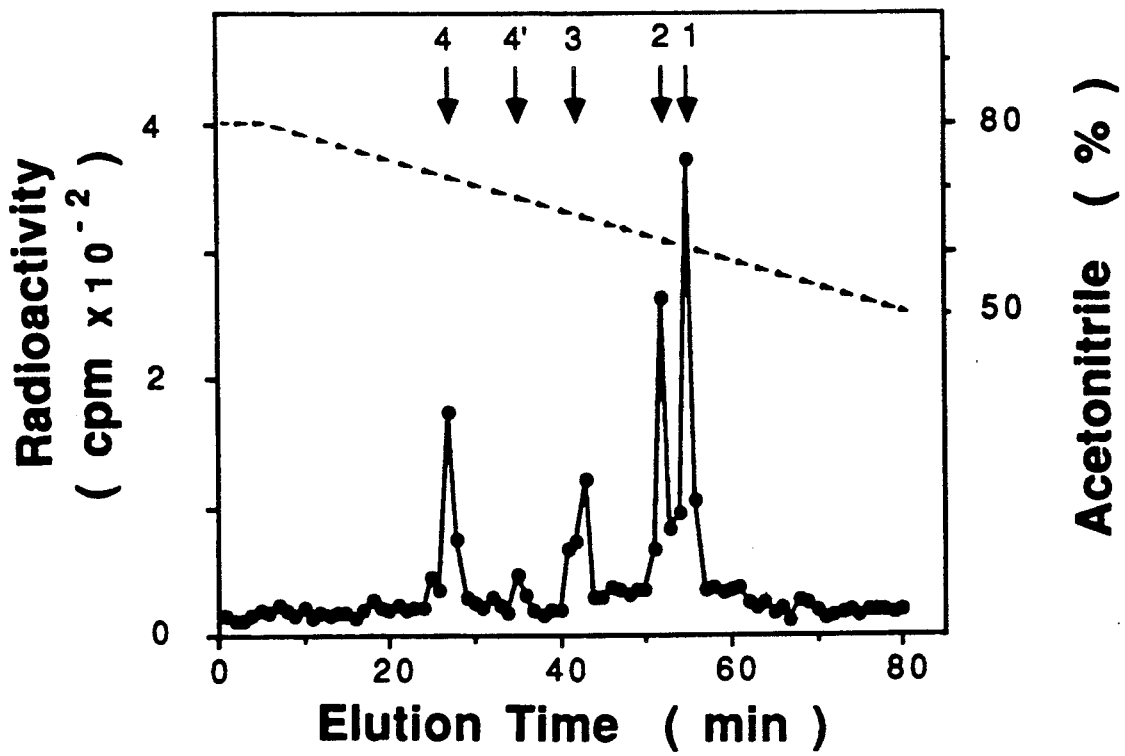

FIGS. 5A and 5B show HPLC analysis of intact O-glycans on amino-bonded silica (Lichrosorb-NH$_2$) column. Oligosaccharides were separated by HPLC on a Lichrosorb-NH$_2$ column as described in Example II. FIG. 5A, O-glycans from T-CLL; FIG. 5B, O-glycans from T-ALL. The elution positions of standard oligosaccharides, as designated in FIGS. 4A-4D, are indicated by arrows, except for 4', Galβ1→3-(NeuNAcα2→6)GalNAcOH. Solid line, radioactivity; dotted line, acetonitrile concentration.

Figure 6A:
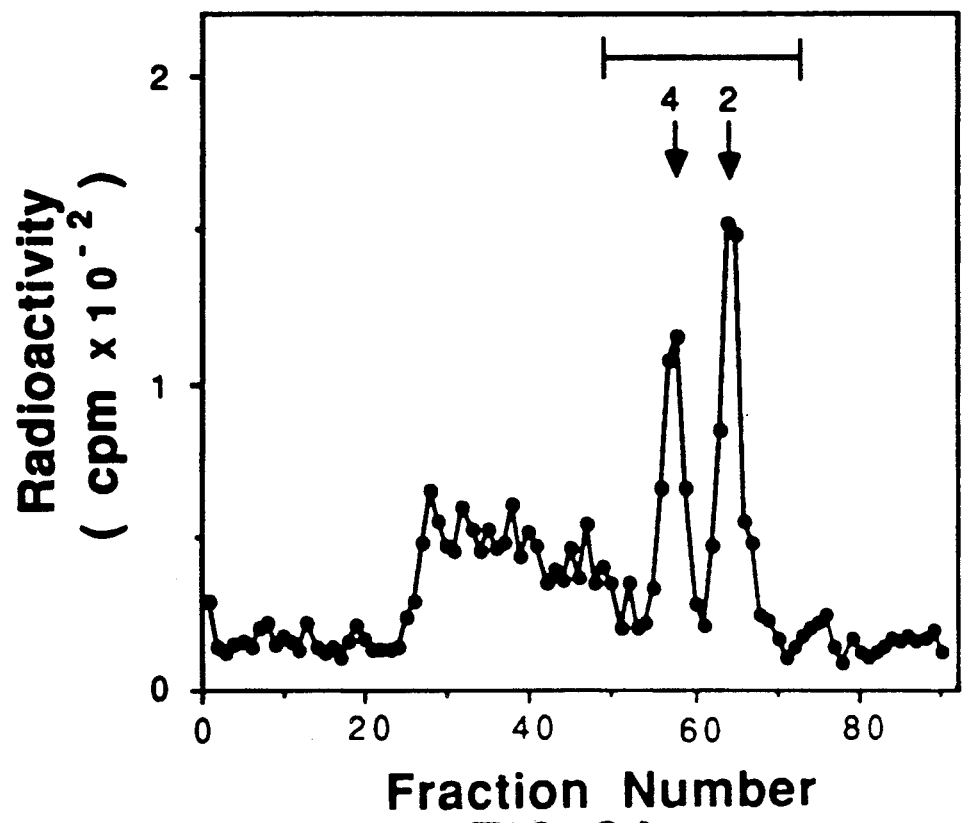
Figure 6B:
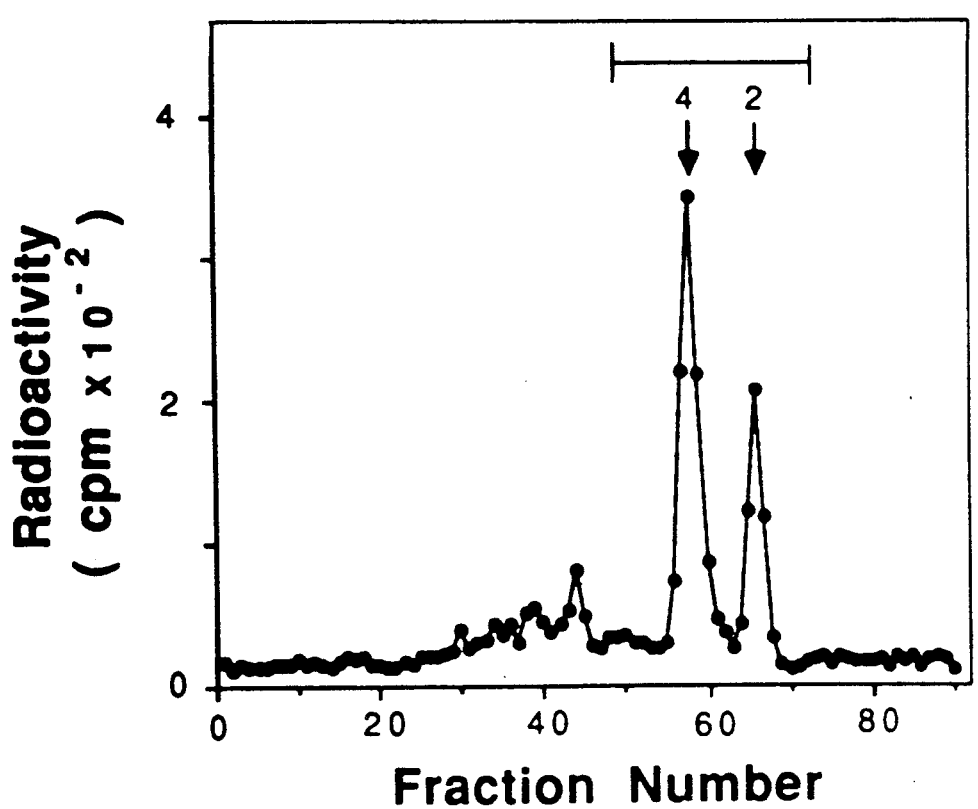
Figure 6C:
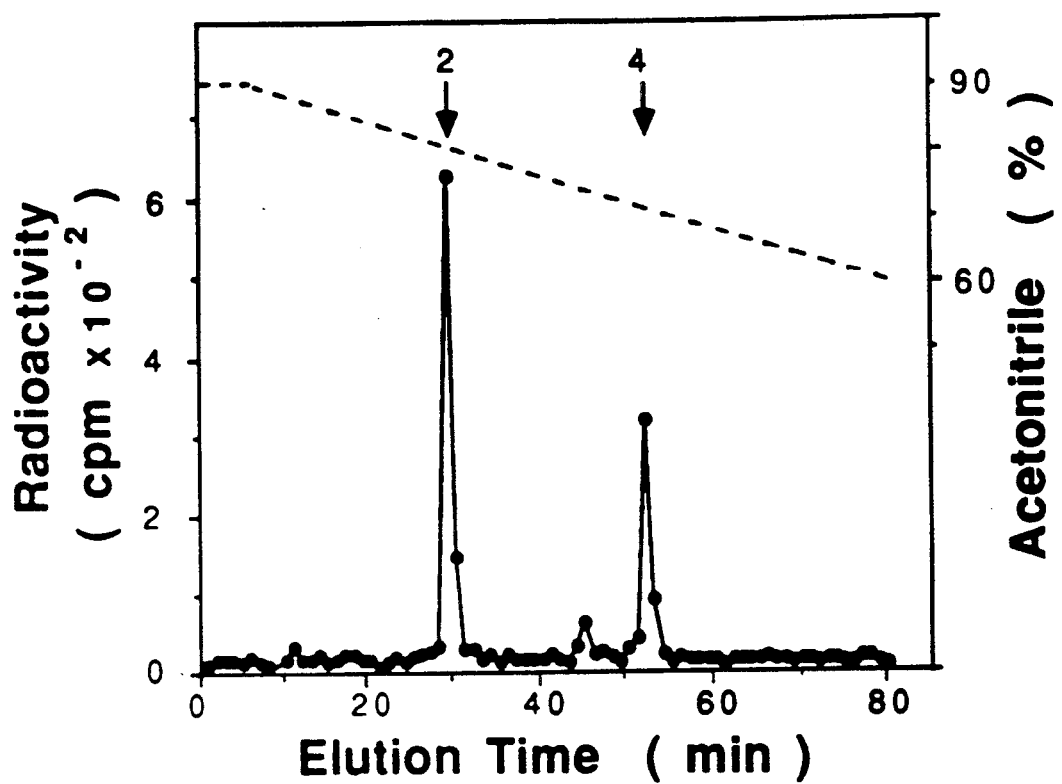
Figure 6D:
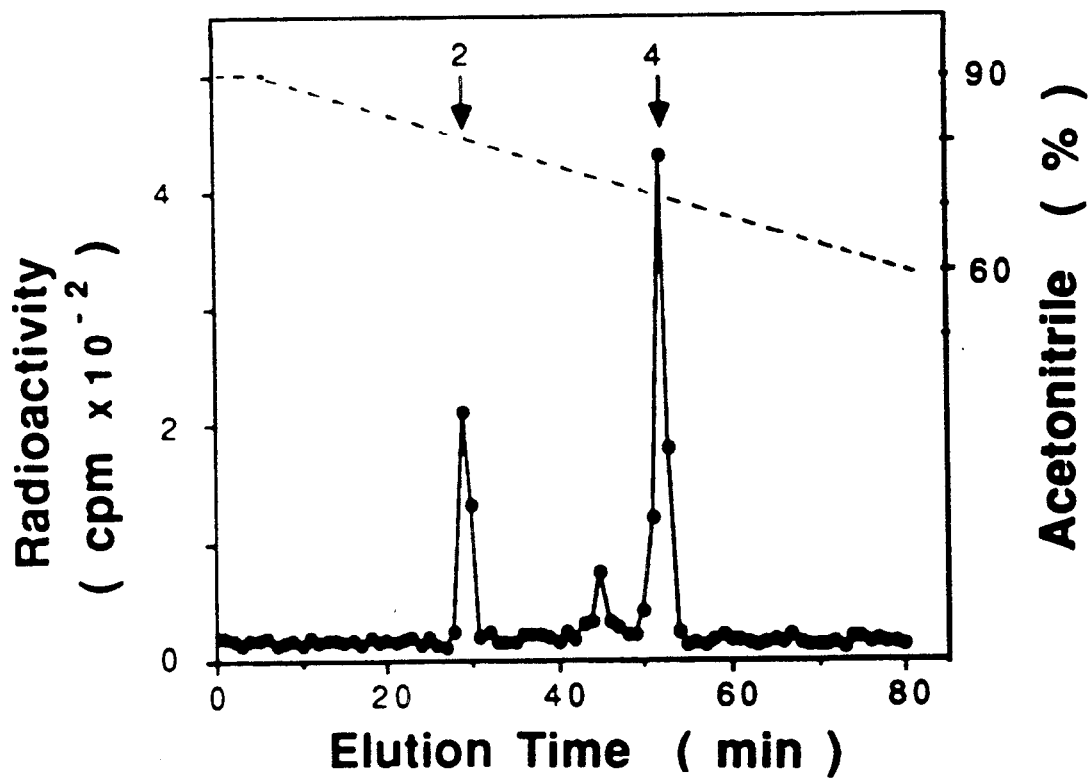
Figure 8A:
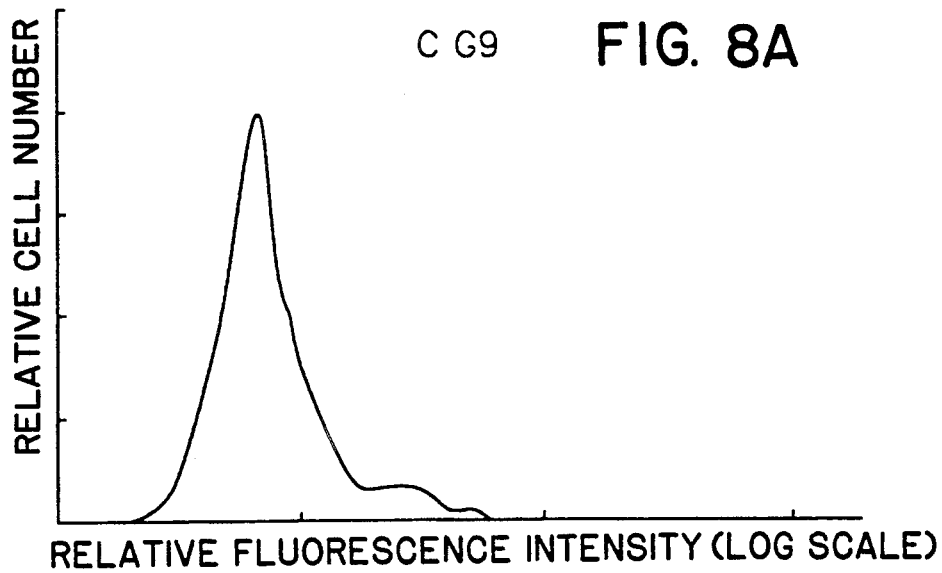
Figure 8B:
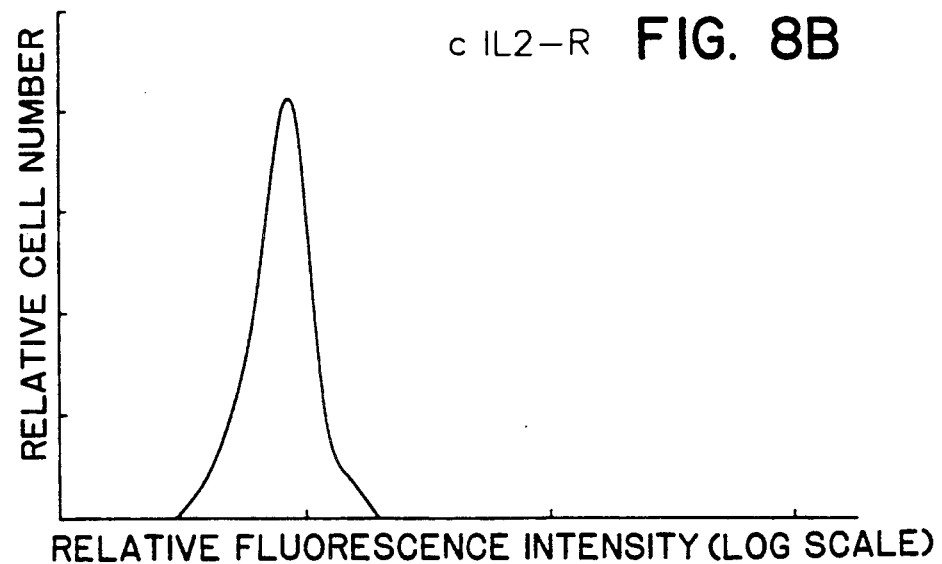
Figure 8C:
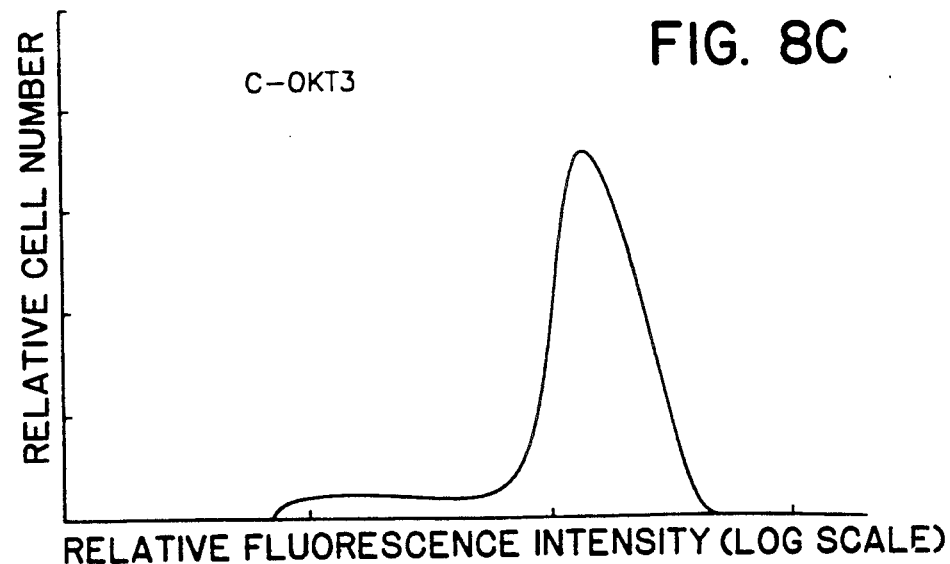
Figure 8D:
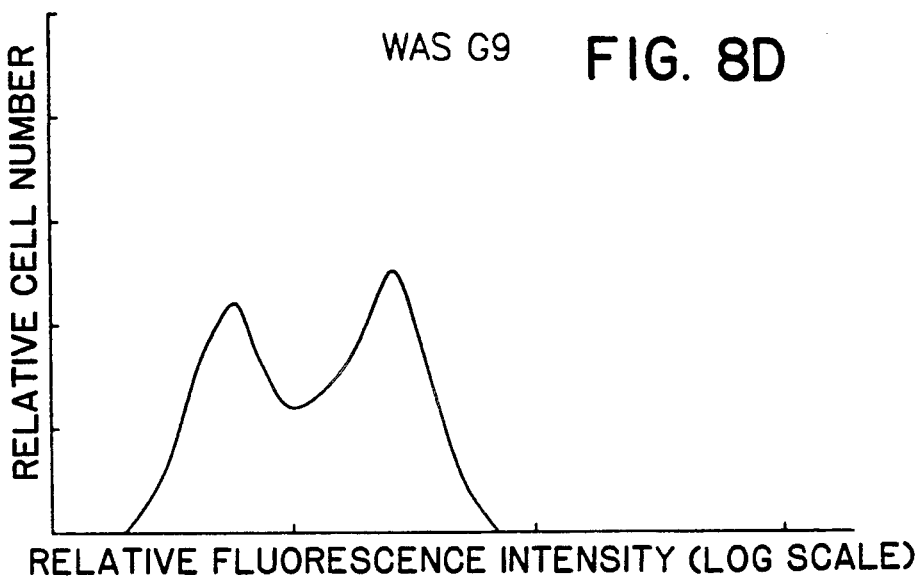
Figure 8E:
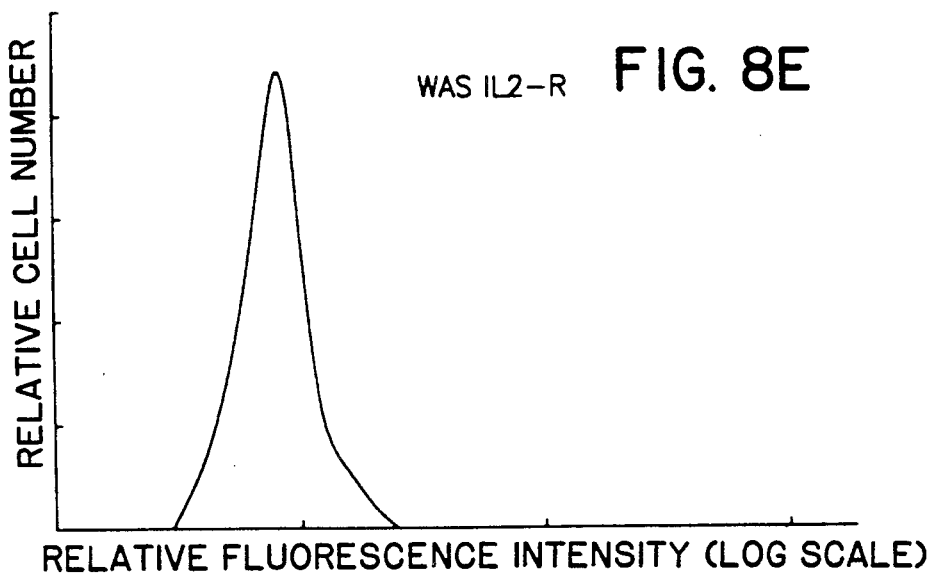
Figure 8F:
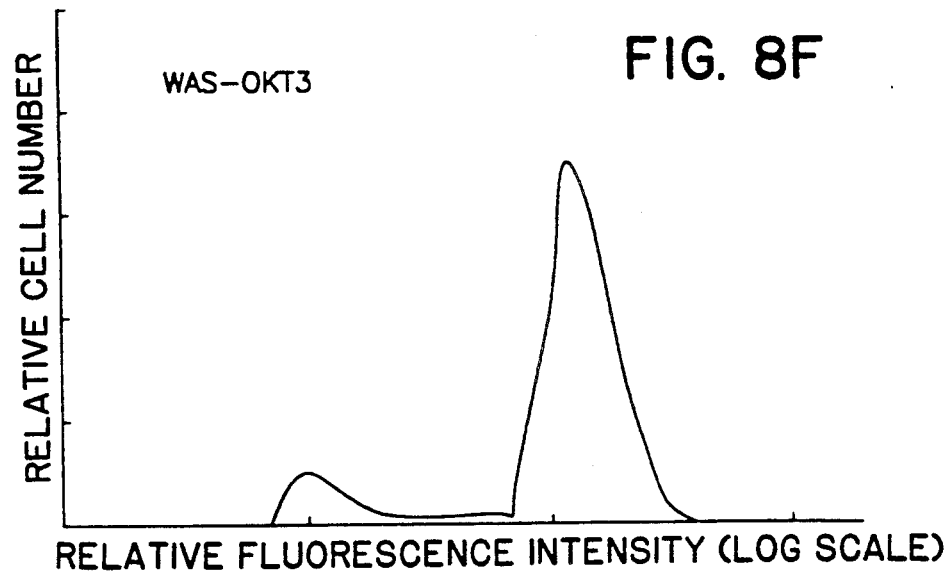
Figure 8G:
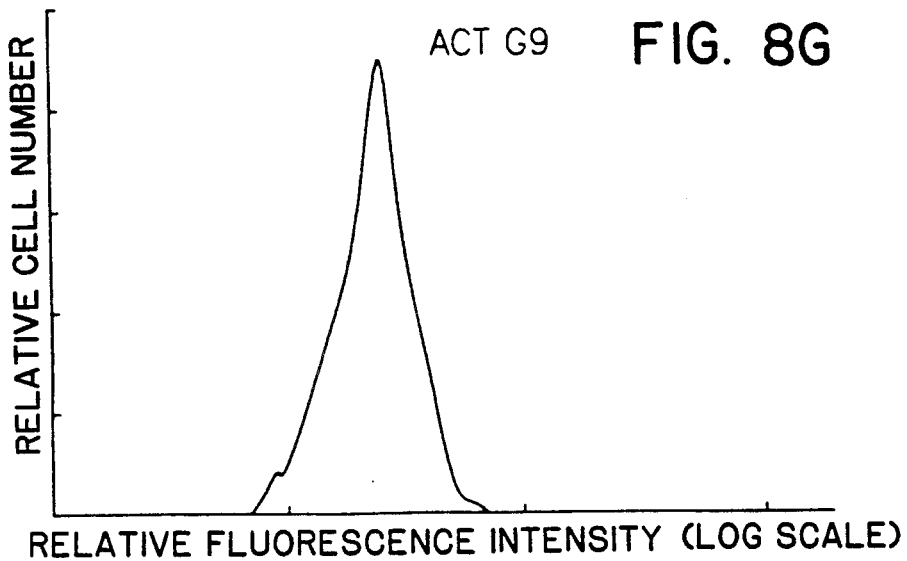
Figure 8H:
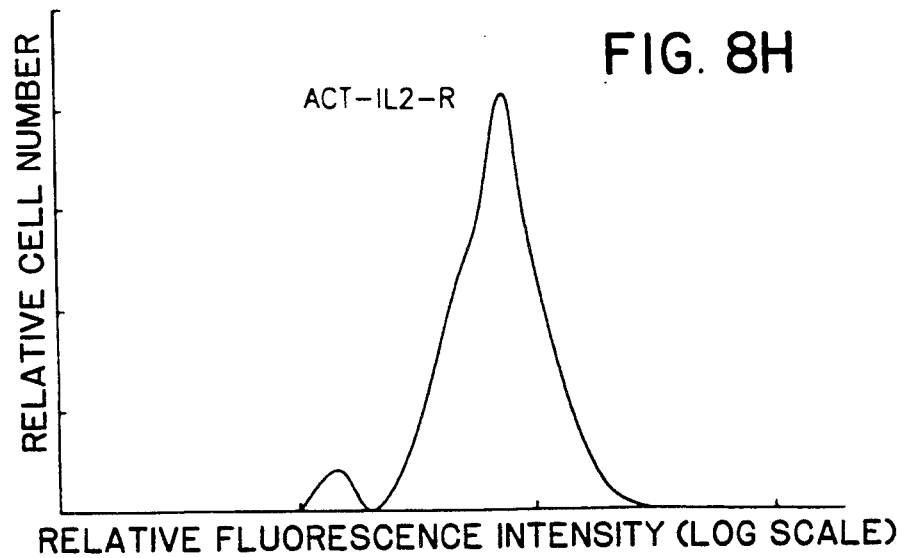
Figure 8I:
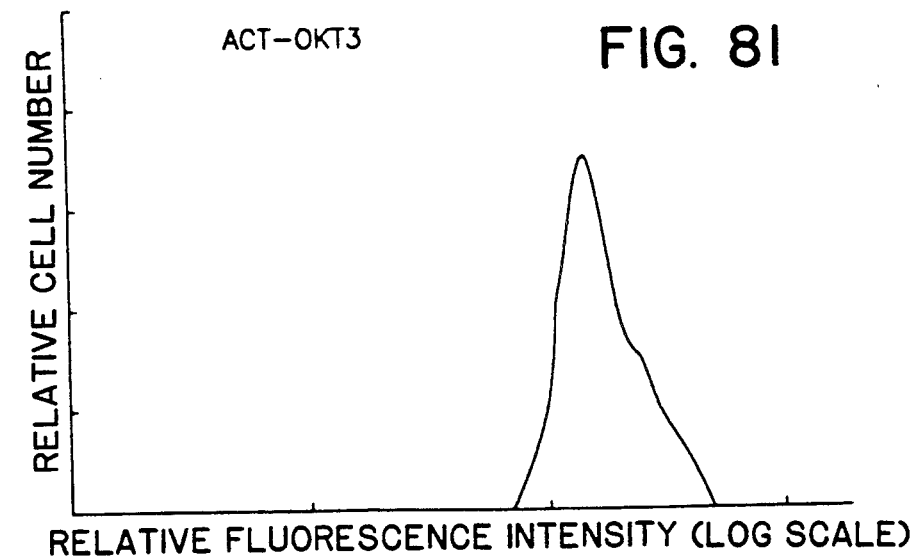

FIGS. 6A and 6B show analysis of O-glycans after removal of sialic acid. FIGS. 6A and 6B, Bio-Gel P-4 gel filtration of neutral oligosaccharides obtained from leukosialin that were labeled by galactose oxidase/NaB[$^3$H]$_4$ procedure. Leukosialin was labeled after neuraminidase treatment of T-CLL cells (6A) or T-ALL cells (6B). Fractions were pooled as indicated by bars and subjected to HPLC analysis. FIGS. 6C and 6D, HPLC analysis of neutral O-glycans shown in 6A or 6B, solid line, radioactivity; dotted line, acetonitrile concentration. Arrows marked 2 and 4 indicate the elution positions of Galβ1→3GalNAcOH and Galβ1→3(Galβ1→4GlcNAcβ1→6)GalNAcOH, respectively. The chromatographic conditions are described in Example II.

FIGS. 7A and 7B show detection of leukosialin by anti-leukosialin antibodies and T-305 monoclonal antibody. Cell lysates were subjected to SDS-polyacrylamide gel electrophoresis, transferred to nitrocellulose filters, and the blots were reacted with specific antibodies. Panel 7A: Immunoblots using rabbit anti-leukosialin peptide antiserum (lanes 1–6) or T-305 monoclonal antibody (lanes 7–12) are shown. The cell lysates in lanes 7–12 are duplicates of lanes 1–6. Lanes 1 and 7, K562 cells; lanes 2 and 8, normal peripheral blood lymphocytes; lanes 3 and 9, T-ALL; lanes 4 and 10, T-ALL, lanes 5 and 11, T-CLL; lanes 6 and 12, HSB-2 cells. Panel 7B: Immunoblots using rabbit anti-leukosialin peptide antiserum. Lane 1, normal PBL; lane 2, T-ALL; lane 3, T-CLL; lane 4, K562 cells; lane 5, HSB-2 cells.

FIGS. 8A–8I show an immunofluorescence analysis of WAS lymphocytes. Cells were analyzed on a flow-cytometer and the fluorescence histograms from normal peripheral blood lymphocytes (8A, 8B, 8C), WAS peripheral blood lymphocytes (8D, 8E, 8F) and activated T-lymphocytes (8G, 8H, 8I) are shown. Indirect immunofluorescence was performed with T305 (clone G9) (8A, 8D, 8G), anti-IL2-Rα(anti-CD25) (8B, 8E, 8H) and OKT-3 (8C, 8F, 8I) as first antibodies and affinity purified, FITC-labeled goat anti-mouse antibodies as second antibodies.

FIGS 9A–9C show Western blots of total cell lysates of WAS lymphocytes. Panel 9A: anti-CD43 anti-leukosialin) antiserum; Lane 1: normal lymphocytes, lanes 2–5: WAS lymphocytes, lane 6: synovial fluid lymphocytes from a patient with rheumatoid arthritis. Panel 9B: T305 (clone G9), same samples as in 9A. Panel 9C: WAS lymphocytes, lane 1: anti-CD43, lane 2: T305.

Figure 10:
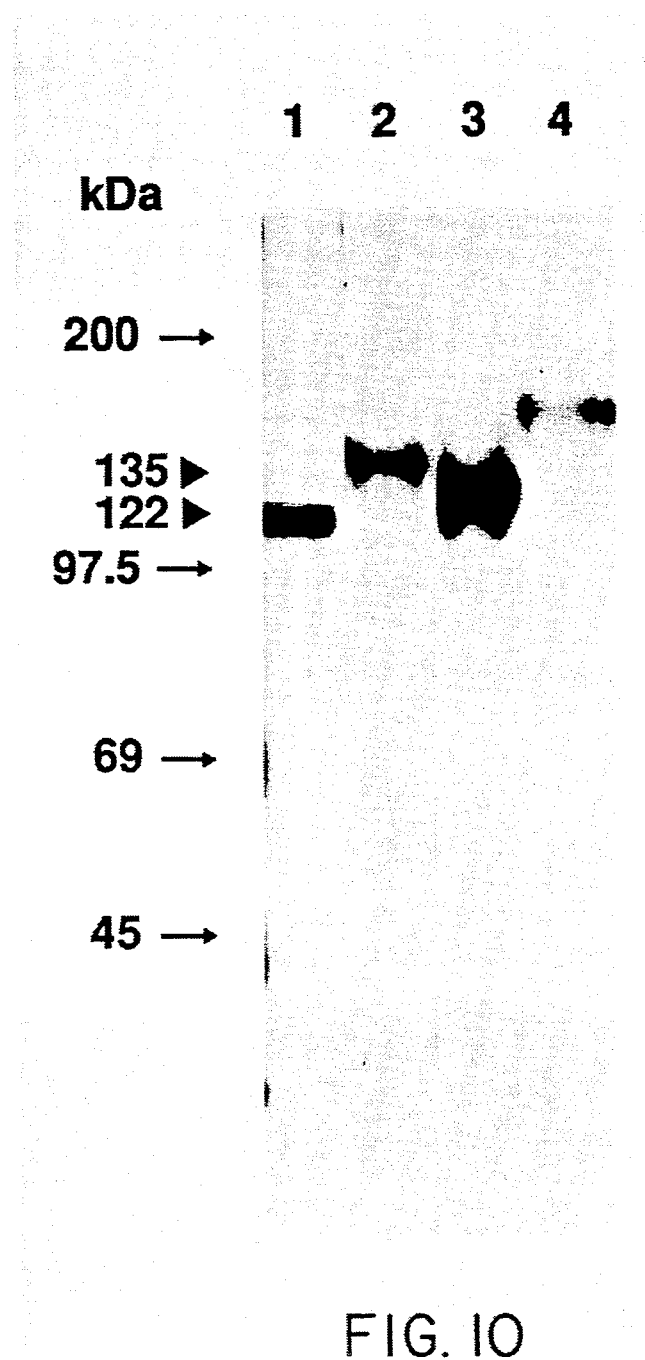
Figure 11A:
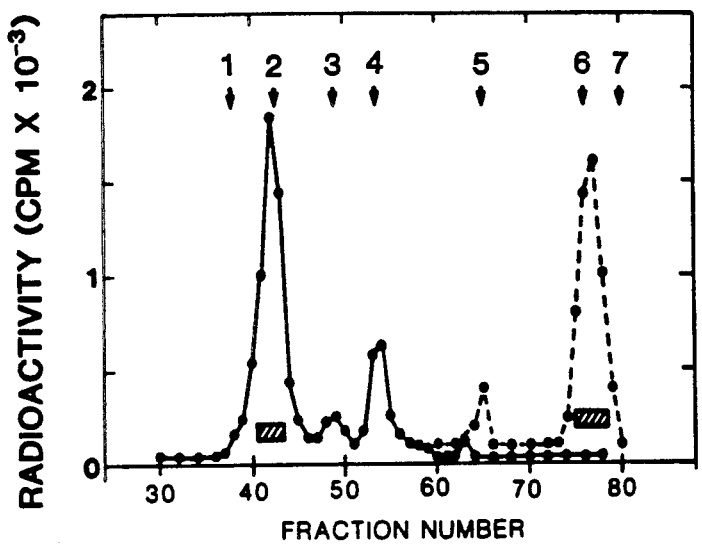
Figure 11B:
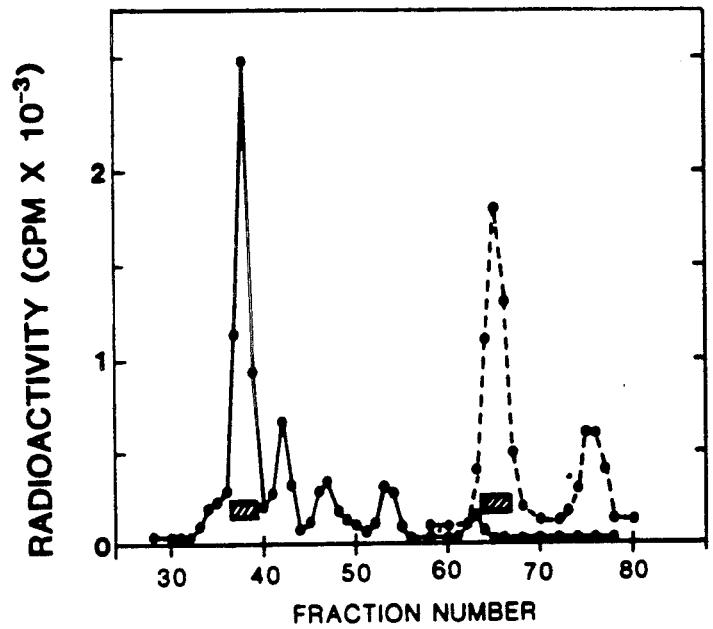
Figure 11C:
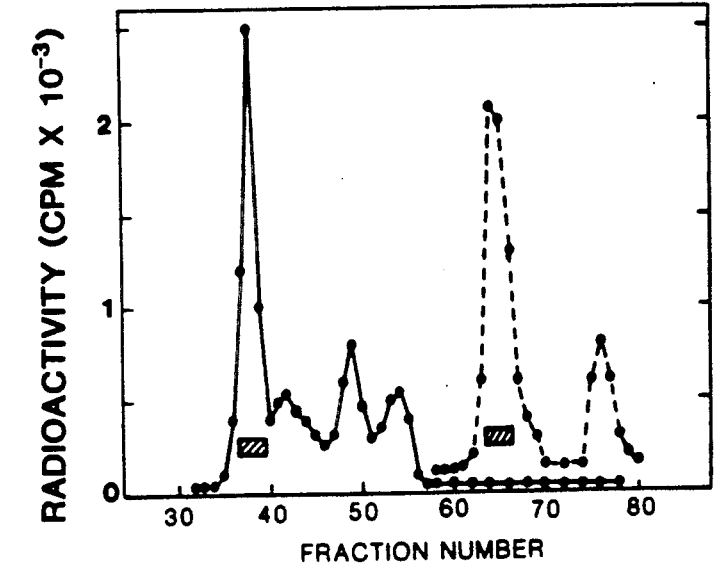
Figure 11D:
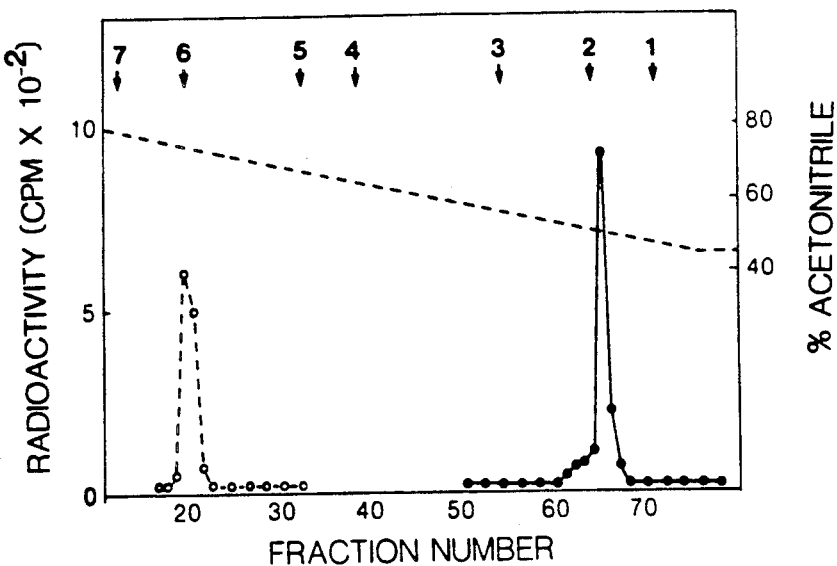
Figure 11E:
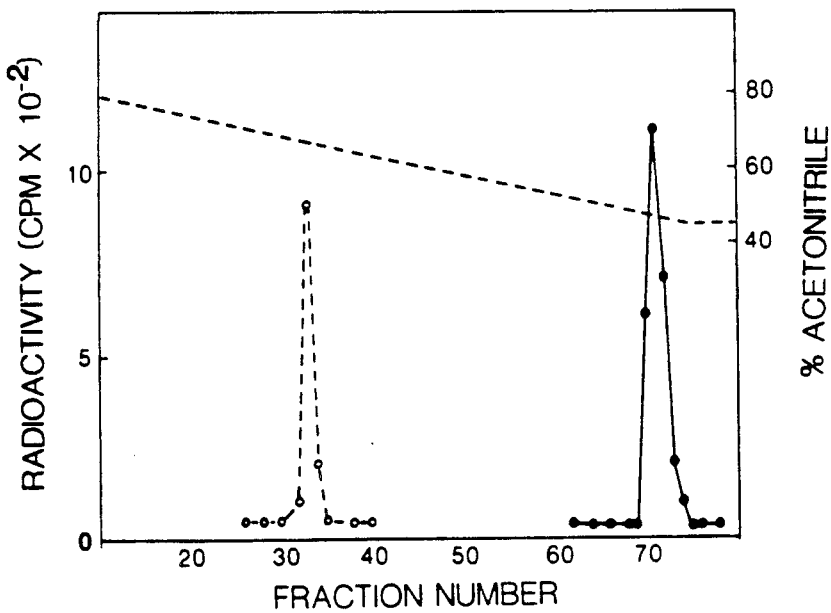
Figure 11F:
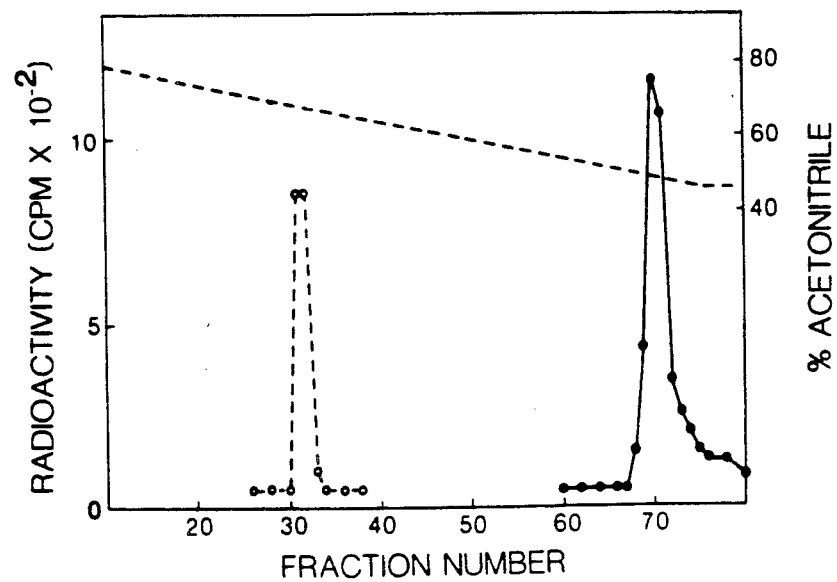

FIG. 10 shows the immunoprecipitation of CD43 (leukosialin) from normal and WAS lymphocytes. The intact cells were labeled by periodate oxidation of sialic acid and reduction with [$^3$H] sodium borohydride or, after removal of sialic acid, by oxidation with galactose oxidase and reduction with [³H] sodium borohydride according to the published procedures. CD43 was immunoprecipitated with the carbohydrate independent antiserum and analyzed on 7% polyacrylamide gels. Lanes 1 and 2 show immunoprecipitates from native and sialidase treated normal lymphocytes, and lanes 3 and 4 native and asialo CD43 from WAS lymphocytes.

FIGS. 11A-11F are a carbohydrate analysis of leukosialin from WAS T-lymphocytes. Lymphocytes were labeled in their cell surface carbohydrates, leukosialin immunoprecipitated, the oligosaccharides were released by alkaline/borohydride treatment and analyzed by gel filtration on Bio-Gel P-4 (11A-11C) and by HPLC on aminobonded silica (Lichrosorb-NH$_2$) (11D-11F). oligosaccharide profiles from unstimulated normal (11A, 11D) and WAS lymphocytes (11B, 11E) and from normal lymphocytes cultured for 5 days in the presence of 50 ng/ml OKT-3 and 50 U/ml IL-2 are shown. ●—● Oligosaccharides from native and ○—○ from neuraminidase treated cells. Fractions marked by the bars ▨ in 11A-11C were pooled and analyzed by HPLC (11D-11F). The numbered arrows indicate the elution positions of oligosaccharide standards:

1: NeuNAcα2→3Galβ1→3(NeuNAcα2→3Galβ1→4GlcNAcβ1→6)GalNAcOH
2: NeuNAcα2→3Galβ1→3(NeuNAcα2→6)GalNAcOH
3: NeuNAcα2→3Galβ1→3(Galβ1→4GlcNAcβ1→6)GalNAcOH and Galβ1→3-(NeuNAcα2→3Galβ1→4GlcNAcβ1→6)GalNAcOH
4: NeuNAcα2→3Galβ1→3GalNAcOH and Galβ1→3(NeuNAcα2→6)GalNAcOH
5: Galβ1→3(Galβ1→4GlcNAcβ1→6)GalNAcOH
6: Galβ1→3GalNAcOH
7: GalNAcOH

DETAILED DESCRIPTION OF THE INVENTION

The invention is directed to a method of detecting T-cell dysfunctions. In one embodiment, T-ALL or WAS is detected by detecting an increased level of leukosialin having the branched hexasaccharide NeuNAcα2→3Galβ1→3(NeuNAcα2→3Galβ1→4GlcNAcβ1→6)GalNAc. Immunoblot analysis with an antibody specific to the hexasaccharide reveals increased levels of leukosialin of high molecular weight in cell lysates from T-ALL and WAS patients compared to normal individuals. Detection of leukosialin having such a hexasaccharide structure is indicative of T-ALL or WAS.

In another embodiment, T-ALL or WAS is detected by detecting an increased level of core 2 GlcNAc transferase. This transferase is a key enzyme in regulating the synthesis of the hexasaccharide found on leukosialin in high levels from T-ALL or WAS subjects. Increased levels of core 2 GlcNAc transferase can be determined by detecting the amount or activity of the enzyme and comparing it to the amount from a normal individual. Detection of such high levels is indicative of T-ALL or WAS.

As used herein, the term "T-cell dysfunction" refers to a defect in the normal biological activity of a T-lymphocyte. A T-cell dysfunction can include, for example, defects involved in antigen recognition, host cell recognition or growth control. Normally, peripheral blood lymphocytes can be in a resting or proliferative state. In the proliferative state, T-cells express certain receptors which are required to perform normal biological functions. An example of such a receptor is the interleukin-2 receptor. A defect in the normal biological activity of a T-cell includes those T-cells which are actively dividing but do not express functional receptors such as the interleukin-2 receptor. T-cell leukemias and immunodeficiencies exhibit these two properties and are therefore included as T-cell dysfunctions. Specific examples of such dysfunctions include acute T-lymphocytic leukemia (T-ALL), chronic T-lymphocytic leukemic (T-CLL), Wiskott-Aldrich Syndrome (WAS) and Acquired Immunodeficiency Syndrome (AIDS).

As used herein, the term "resting T-cells" refers to peripheral blood T-lymphocytes which are not active and also do not express the interleukin-2 receptor.

The invention provides a method of detecting T-cell dysfunctions which includes detecting an alteration in the level of a protein regulating synthesis of the hexasaccharide NeuNAcα2→3Galβ1→3(NeuNAcα2→3Galβ1→4 GlcNAcβ1→6)GalNAc on leukosialin of T-cells from a subject suspected of having a T-cell dysfunction compared to resting T-cells from a normal individual. The T-cell dysfunction can be, for example, Wiskott-Aldrich Syndrome. T-cell dysfunctions other than Wiskott-Aldrich Syndrome can also be detected by the methods provided herein. Such T-cell dysfunctions include, for example, acute T-lymphocytic leukemia and chronic T-lymphocytic leukemia. The invention also provides a method of detecting T-cell dysfunctions which includes detecting an alteration in the level of leukosialin having the hexasaccharide NeuNAcα2→3Galβ2→3(NeuNAcα2→3 Galβ1→4GlcNAcβ1→6)GalNAc on T-cells from a subject suspected of having a T-cell dysfunction compared to resting T-cells from a normal individual.

The present invention will be described with reference to T-cell dysfunctions of leukemic origin. However, one skilled in the art can use the teachings described herein to detect T-cell dysfunction of other origins such as immunodeficiencies. Leukemic cells of T-cell origin express O-glycans that are more complex than those expressed on resting T-lymphocytes. Due to the presence of this more complex hexasaccharide, the apparent molecular weight of leukosialin becomes greater in leukemic cells. In addition, all glycoproteins detected by a monoclonal antibody specific to the hexasaccharide are larger than those detected in resting T-lymphocytes by anti-leukosialin antibodies. These results indicate that leukosialin can be determined to contain the hexasaccharides when it has a high molecular weight and reacts with a hexasaccharide specific antibody.

The appearance of the branched hexasaccharide is caused by the presence of Galβ1→3GalNAc:β1→6N-acetylglucosaminyltransferase (core 2 GlcNAc-T). This same enzyme is critical in the conversion of the tetrasaccharides to the hexasaccharides during T-cell activation and thus is responsible for regulating the synthesis of the hexasaccharide. Core 2 GlcNAc-T is essential to form Galβ1→3(GlcNAcβ1→6)GalNAc, which in turn is changed into Galβ1→3(Galβ1→4GlcNAcβ1→6)GalNAc by β-galactosyltransferase, and then to the final product, NeuNAcα2→3Galβ1→3-(NeuNAcα2→3Galβ1→4GlcNAcβ1→6)GalNAc, by the action of α2→3sialytransferases. Unlike that of activated lymphocytes, the activity of α2→6sialyltransferase is not changed in leukemic cells. Conversion to the hexasaccharide is probably due to its presence in earlier Golgi cisternae than α2→6sialyltransferase. In this case, core 2 GlcNAc-T adds N-acetylglucosamine at C-6 of N-acetylgalactosamine before the α2→6sialyltransferase adds a sialic acid to the same position. The branched hexasaccharide is therefore formed by β1→6N-acetylglucosaminyltransferase regardless of whether α2→6sialyltransferase is present or not.

Detection of such altered core 2 GlcNAc-T levels or hexasaccharide levels provides a basis for diagnosis and prognosis of leukemia of T-cell origin. When a patient's leukemic cells are found to express predominantly high molecular weight leukosialin compared to a normal individual, that patient must be suspected to have a significant number of T-lymphoblastoid cells. In addition, when a patient with T-CLL exhibits the high molecular weight form of leukosialin, the proportion of lymphoblasts increase in peripheral blood lymphocytes. These results indicate that the prognostic status of a patient can be assessed by determining the molecular weight of leukosialin and its reactivity with hexasaccharide specific antibodies. Thus, the invention provides a method of detecting T-cell dysfunctions by determining the amount of binding to a specific ligand, such as an antibody.

Alternatively, the prognostic status of a subject can be assessed by determining the levels of a protein regulating synthesis of the hexasaccharide structure and comparing it to that obtained from resting T-cells of a normal individual. As previously described, core 2 GlcNAc-T is the key enzyme regulating the synthesis of the hexasaccharide structure described herein. The levels of core 2 GlcNAc-T can be assessed by either determining the amount of the enzyme or the activity of the enzyme. Activity can be determined by a simple enzymatic assay using a substrate which is detectable once converted to product. Likewise, levels of a protein which regulates the synthesis or activity of core 2 GlcNAc-T can also be assessed for determining an alteration in the levels of a protein regulating synthesis of the hexasaccharide structure. The amount of core 2 GlcNAc-T, for example, can be determined by binding a ligand and determining the amount of binding. Ligands can be, for example, antibodies or substrate analogues such as Galβ1→3GalNAc attached to agarose. The bound ligands are detected using methods known to one skilled in the art. Such methods include, for example, Western blots, immunoprecipitations and ELISA and are described in Antibodies: A Laboratory Manual, Harlow et al., Cold Spring Harbor Laboratories, Cold Spring Harbor, N.Y. (1989), which is incorporated herein by reference. Thus, the invention provides a method of detecting T-cell dysfunctions by detecting an increased activity of core 2 GlcNAc-T as well as a method of detecting which includes binding core 2 GlcNAc-T with a ligand and determining the amount of binding. The ligand can be an antibody or a substrate analogue.

Also provided is a kit for the detection of a T-cell dysfunction. The kit includes a detecting reagent and ancillary reagents. "Detecting reagents" as used in reference to a kit are those reagents which can be used to determine the amount or activity of a protein regulating synthesis of the hexasaccharide NeuNAcα2→3Galβ1→3(NeuNAcα2→3Galβ1→4GlcNAcβ1→6)GalNAc or those reagents which can be used to determine the amount of leukosialin having the above hexasaccharide. Such reagents have been previously described and can be provided in a kit for the detection of T-cell dysfunctions. For example, if the activity of core GlcNAc-T is to be measured for detecting a T-cell dysfunction, then the detecting reagent can be a substrate having, for example, a labeled moiety which can be detected once converted to product. Alternatively, if the amount of core 2 GlcNAc-T is to be measured then a ligand which binds this enzyme can be used as a detecting reagent. The ligand can be, for example, an antibody or a substrate analogue. Similarly, a ligand such as an antibody can also be used to detect the amount of leukosialin having the hexasaccharide structure.

Ancillary reagents which can also be included in the kit can include buffers for binding and detecting such detecting reagents. Control samples, such as cell lysates from a normal individual, can also be included as ancillary reagents.

The following examples are intended to illustrate but not limit the invention.

EXAMPLE I

Analysis of Leukosialin from Various Leukemic Cells by SDS-polyacrylamide Gel Electrophoresis This example shows that leukosialin from T-ALL has a higher apparent molecular weight than leukosialin from T-CLL and that the apparent molecular weight of leukosialin from T-CLL is slightly higher than that of leukosialin from a normal individual.

Human erythroleukemia K562 and promyelocytic leukemia HL-60 and T-lymphoblastoid HSB-2 were cultured in RPMI 1640 medium supplemented with 10% fetal calf serum and 2 mM glutamine. Lymphocytes from the peripheral blood of normal individuals and patients were prepared by centrifugation in Histopaque-1077 (Sigma, St. Louis, Mo.). The peripheral blood (~5 ml) was carefully overlayed on the Histopaque solution (~5 ml) in a 15 ml centrifuge tube. After centrifugation at 800 xg for 10 minutes, the lymphocytes at interphase between Histopaque and plasma were collected by using a pasteur pipet. Human thymocytes were obtained when a thymus was removed surgically for cardiac surgery. In total, 16 cases of acute T-lymphocytic leukemia (T-ALL) and 6 cases of chronic T-lymphocytic leukemia (T-CLL) were subjected to analysis.

Sialic acid residues on the cell surface were labeled by sodium periodate oxidation followed by $NaB[^3H]_4$ reduction. Galactose and N-acetylgalactosamine residues on the cell surface were labeled by the galactose oxidase/$NaB[^3H]_4$ method after treatment with *Vibrio cholerae* neraminidase. The former method labels the intact sialic acid-containing oligosaccharides whereas the latter method reveals the neutral, backbone oligosaccharides remaining after removal of sialic acid. Carbohydrates of leukemic cell lines were metabolically labeled with [$^3H$]-glucosamine. Briefly, cells were incubated with glucose-free RPMI 1640 medium with 10% dialyzed fetal calf serum and 2 mM glutamine, complemented with 5% complete RPMI 1640 medium containing 10% fetal calf serum and 2 mM glutamine. [$^3H$]-Glucosamine (30 Ci/mmole, Du Pont-New England Nuclear, Boston, Mass.) was added at 10 μ Ci/ml, and the cells were labeled for 18h at 37° C.

After each labeling, the cells were harvested and washed twice with phosphate buffered saline (PBS)/EDTA, lysed with PBS containing 1% NP-40 in the presence of 1 mM phenylmethylsulfonyl fluoride, 1

μg/ml of each leupeptin and aprotinin and 5 mM of sodium tetrathionate as protease inhibitors. The supernatant, after brief centrifugation, was used as a total cell lysate. Leukosialin was immunoprecipitated by rabbit anti-leukosialin serum, which was kindly provided by Dr. Sven Carlsson, followed by the addition of *Staphylococcus aureus* (Pansorbin, Calbiochem, La Jolla, Calif.). Aliquots of the immunoprecipitates were analyzed by SDS-polyacrylamide gel electrophoresis (8% acrylamide gels) and visualized by fluorography after treatment with Enlightning (Du Pont-NEN, Boston, Mass.).

Leukosialin from K562 cells contain almost exclusively the tetrasaccharide NeuNAcα2→3Galβ1→3-(NeuNAcα2→6)GalNAc expressed on resting T-lymphocytes. The HSB-2 leukemic cell line contains mainly the more complex hexasaccharide NeuNAcα2→3Galβ1→3(NeuNAcα2→3 Galβ1→4GlcNAcβ1→6-)GalNAc, expressed on activated T-lymphocytes. K562 cells and HSB-2 cells were therefore used as markers for low molecular weight and high molecular weight forms of leukosialin, respectively.

FIGS 1A-1B show a fluorogram of leukosialin from various leukemic cells after SDS-gel electrophoresis. The results indicate that leukosialin from T-ALL has a higher apparent molecular weight than leukosialin from T-CLL (FIG. 1A). The apparent molecular weight of leukosialin from T-CLL (lanes 7 and 8) is slightly higher than that of leukosialin from a normal individual (lane 10). The difference in leukosialin molecular weight can be observed even after sialic acid residues are removed. After this treatment, leukosialin from T-ALL cells showed apparent molecular weights similar to leukosialin of HSB-2 cells (FIG. 1B, lane 5). In contrast, leukosialin from T-CLL is heterogenous in molecular weight, migrating at the positions between K562 leukosialin and T-ALL leukosialin (FIG. 1B, lane 4). The same results were obtained on all 16 cases of T-ALL, and all 6 cases of T-CLL. These results indicate that leukosialin from T-CLL contains more complex saccharides than normal T-lymphocytes, and T-ALL contains more of complex saccharides than T-CLL.

Figure 2:
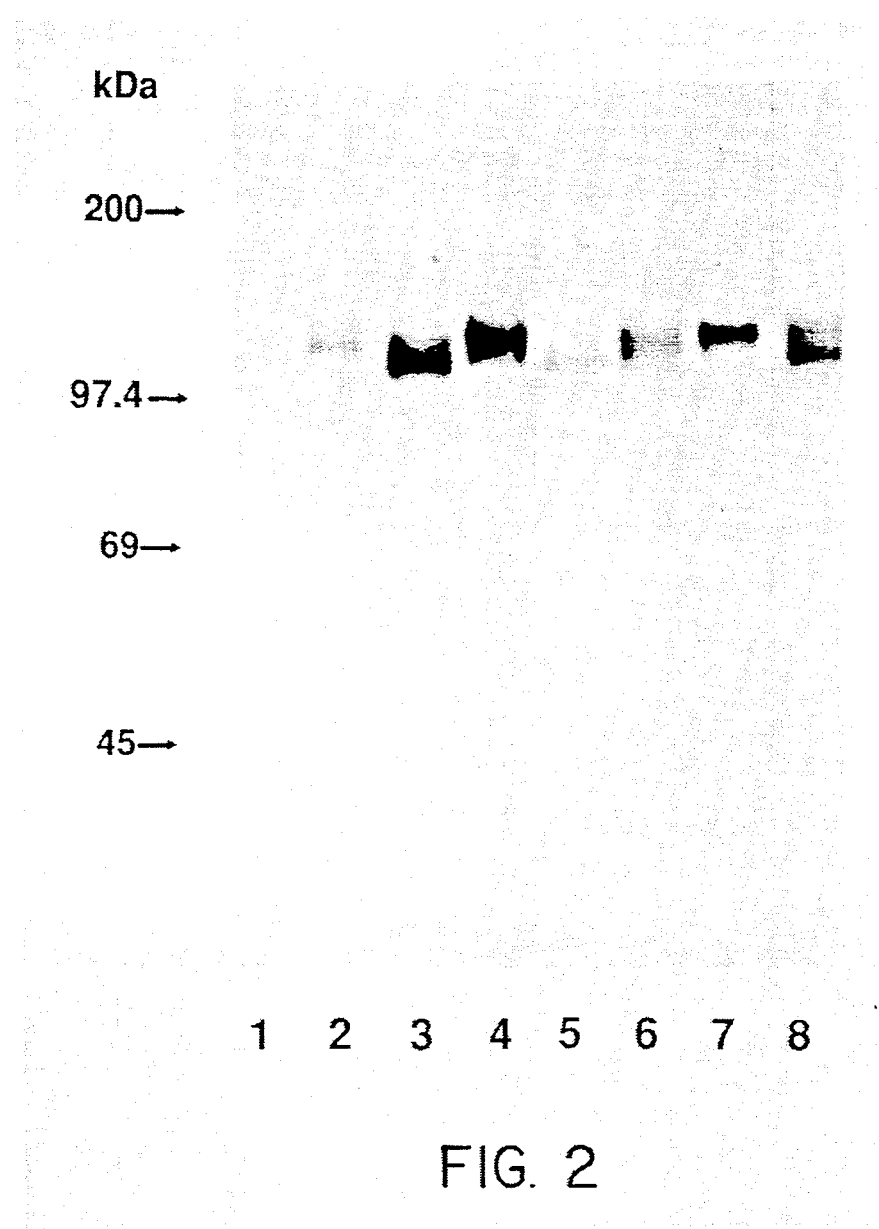
FIG. 2 shows leukosialin immunoprecipitated from various cells after cell surface labeling by periodate oxidation followed by NaB[$^3$H]$_4$ reduction. Immunoprecipitates were analyzed by SDS-polyacrylamide gel electrophoresis followed by fluorography as shown in FIGS. 1A and 1B. Leukosialin labeled at sialic acid residues from B-chronic lymphocytic leukemia (lane 1), hairy cell leukemia (lane 2), T-lymphoma (lane 4), patients infected with HIV with no symptom (lane 5) or with symptoms (lane 6), and synovial fluid T-lymphocytes of an arthritis patient (lane 7). Lanes 3 and 8 are leukosialin expressed on peripheral T-lymphocytes of a normal individual (lane 3) and thymocytes (lane 8).

FIG. 2 shows the fluorogram of leukosialin from other lymphoblastoid diseases. Patients with T-lymphoma, hairy cell leukemia and Acquired Immunodeficiency Syndrome exhibit higher molecular weights than leukosialin from normal individuals. B-lymphocytic leukemia expresses a small amount of leukosialin, although its molecular weight is close to that found in normal T-lymphocytes (compare lanes 1 and 3). It is also noteworthy that an HIV positive patient with no symptoms expresses a low molecular weight form of leukosialin (lane 5), whereas an AIDS patient expresses a high molecular weight form of leukosialin (lane 6).

EXAMPLE II

Structures of O-glycans Attached to Leukosialin on Leukemic Cells

This example shows the O-linked oligosaccharide structures found on T-ALL and T-CLL.

To elucidate the cause of differences observed in molecular sizes of leukosialin, O-glycans attached to leukosialin were analyzed in two typical types of leukemia, T-ALL and T-CLL. Cell surface carbohydrates were labeled by the periodate/NaB[$^3$H]$_4$ procedure and leukosialin was immunoprecipitated as described in Example I. The samples shown in FIG. 1A, lanes 4, 5 and 7, were digested by pronase and the digests were separately applied to a column of Sephadex G-50.

Figure 3A:
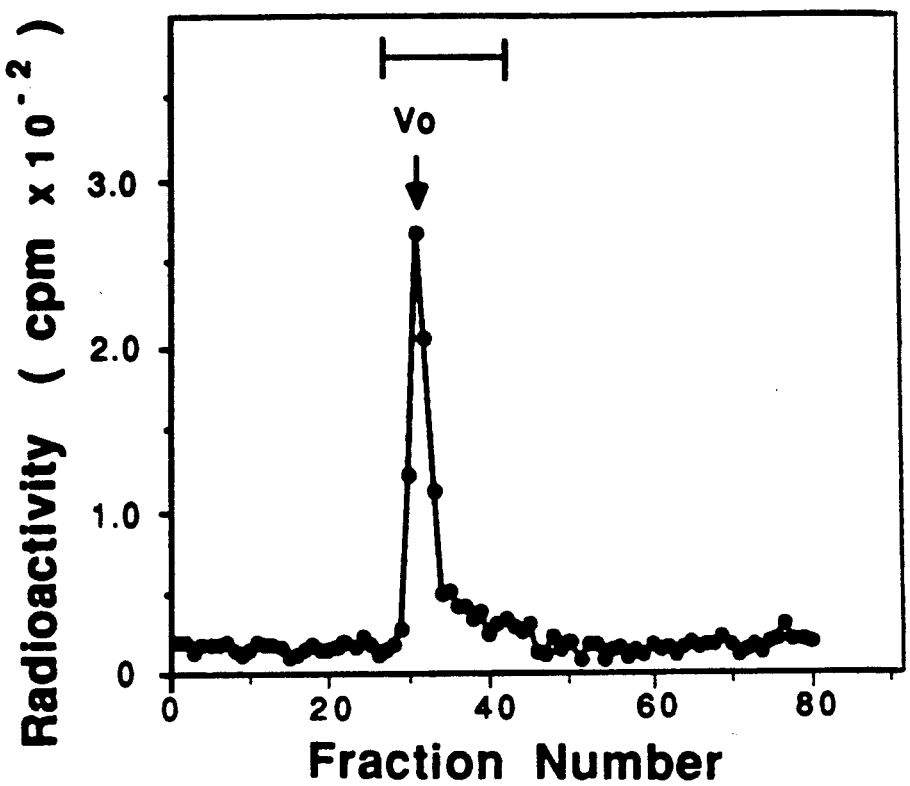
FIGS. 3A–3D show Sephadex G-50 gel filtration of glycopeptides from leukosialin labeled by NaIO$_4$/NaB[$^3$H]$_4$ procedure.
Figure 3B:
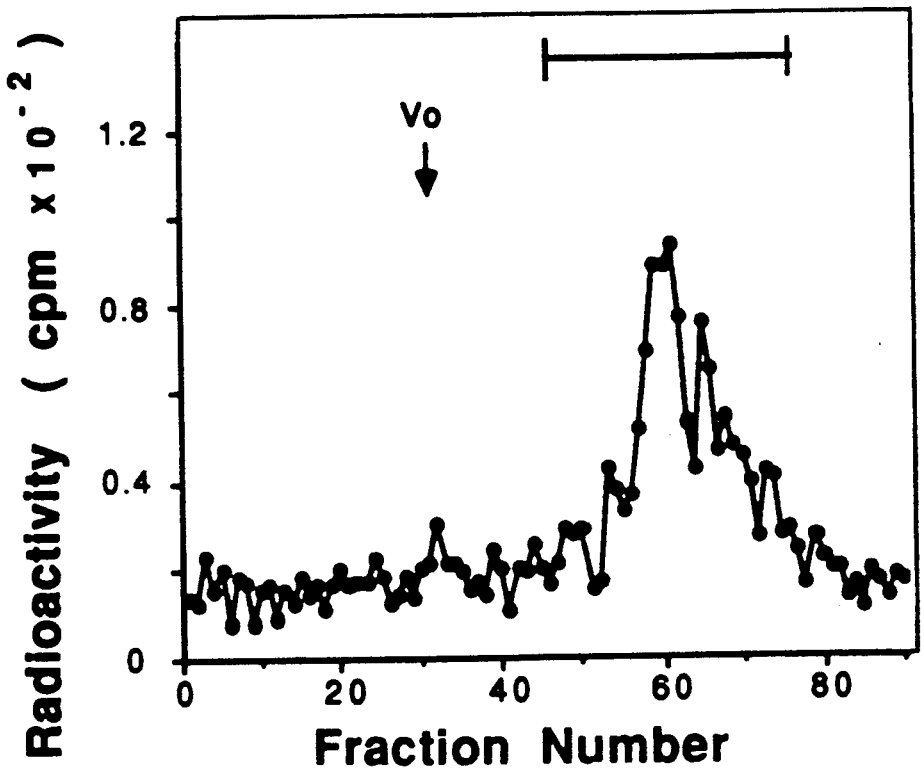
Figure 3C:
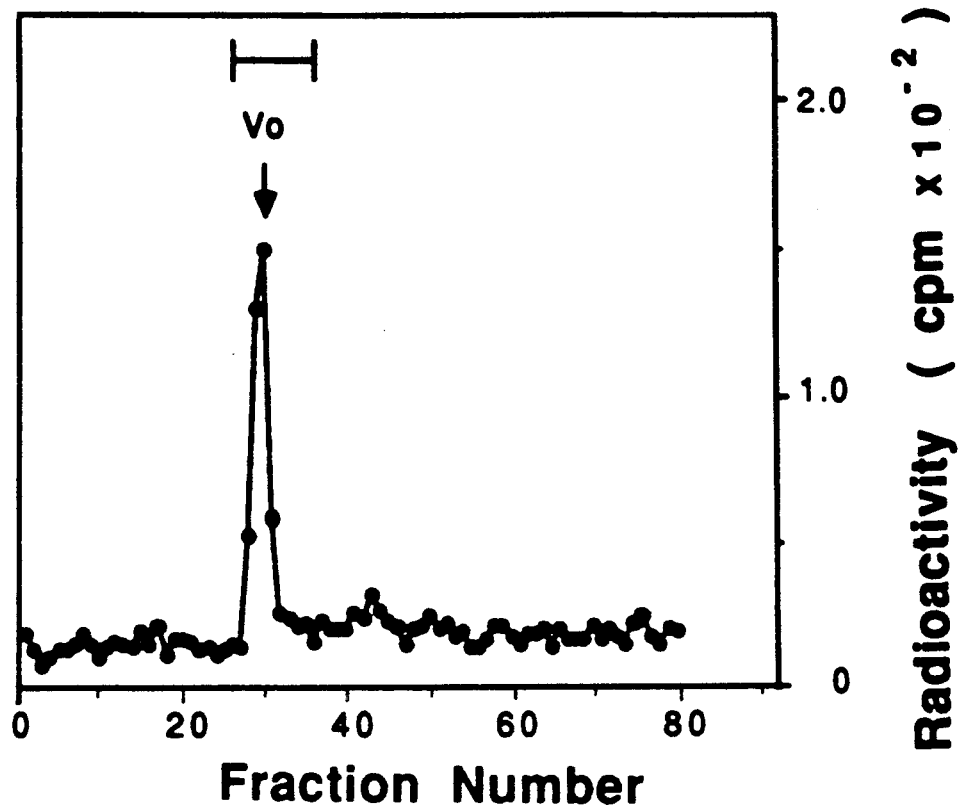
Figure 3D:
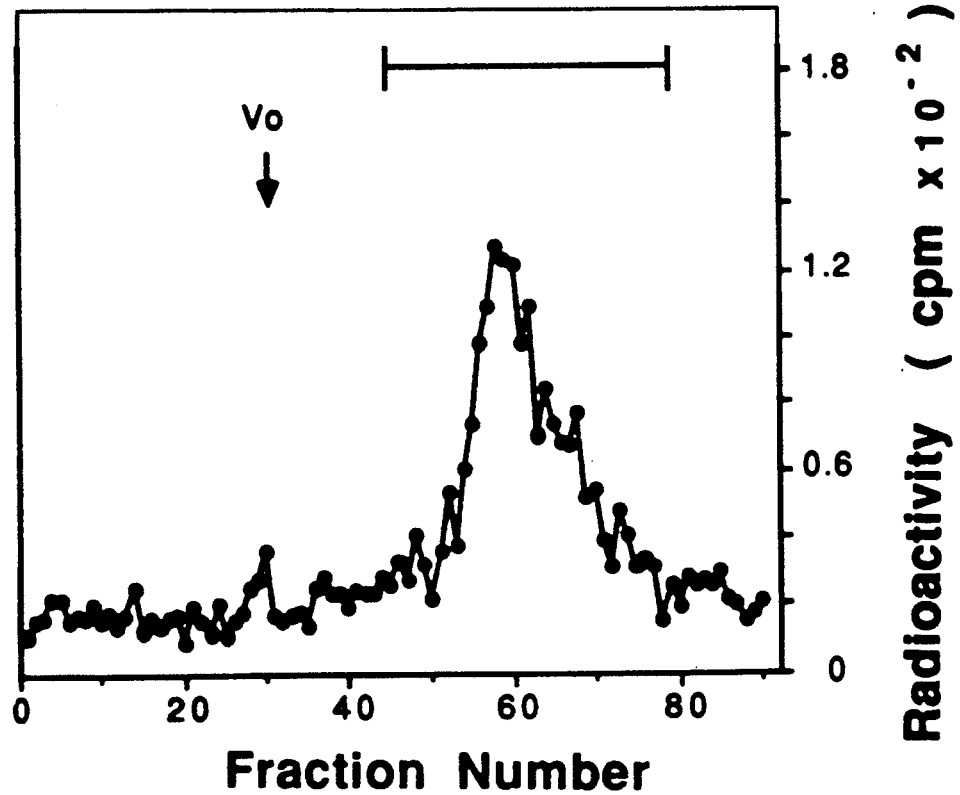

The immunoprecipitates were digested with Pronase (nuclease-free, Calbiochem), and the large glycopeptides were isolated by gel filtration on Sephadex G-50 (Pharmacia, Piscataway, N.J.) as described by Carlsson et al., J. Biol. Chem. 261:12787 (1986), which is incorporated herein by reference. The column was 1.0×110 cm and 1.1 ml was collected for each fraction at a flow rate of 6 ml/hour. FIG. 3A and C show the digested glycopeptides eluted near the void volume of the column. The O-glycans were released from these large glycopeptides by alkaline borohydride treatment as described by Carlsson, D. M., J. Biol. Chem. 243:616 (1968), which is incorporated herein by reference, and isolated by gel filtration on Sephadex G-50 (FIG. 3B and D). The released oligosaccharides were then applied to a column (1.0×108 cm) of Bio-Gel P-4 (−400 mesh; Biorad, Richmond, Calif.). The flow rate was 3 ml/h and each fraction contained 1.0 ml. Both Sephadex G-50 and Bio-Gel P-4 were equilibrated with 0.1M NH$_4$HCO$_3$. The oligosaccharides separated by Bio-Gel P-4 were then analyzed by HPLC on a column (0.4×25 cm) of amino-bonded silica (Lichrosorb-NH$_2$, Merck), using a Varian 5000 HPLC apparatus. The mobile phase was 3% acetic acid in a mixture of acetonitrile/H$_2$O, titrated to pH 5.5 with triethylamine and the flow rate was 1.0 ml/minute. For sialylated oligosaccharide analysis, the composition of mobile phase was isocratic at 80% acetonitrile for 5 minutes, followed by a gradient to 50% acetonitrile in 75 minutes. For separation of neutral oligosaccharides, the composition of the mobile phase was isocratic for 5 minutes at 90% acetonitrile followed by a gradient to 60% acetonitrile in 75 minutes. Standard oligosaccharides were obtained from leukosialin present in HL-60 and K562 cells.

FIG. 4A illustrates that major O-glycans from T-CLL leukosialin elute from the Bio-Gel P-4 column at positions corresponding to the disialylated tetrasaccharide, NeuNAcα2→3Galβ1→3(NeuNAcα2→6)GalNAcOH, and to monosialylated trisaccharide. The latter could be resolved into two isoforms, NeuNAcα2→3Galβ1→3GalNAcOH and Galβ1→3(NeuNAcα2→6-)GalNAcOH, by HPLC chromatography on Lichrosorb-NH$_2$ (FIG. 5A). The disialylated hexasaccharide, NeuNAcα2→3Galβ1→3(NeuNAcα2→3Galβ1→4GlcNAcβ1→6)GalNAcOH, and the monosialylated pentasaccharide, NeuNAcα2→3Galβ1→3(Galβ1→4GlcNAcβ1→6) GalNAcOH, were detected as minor oligosaccharides. In contrast, the major oligosaccharide from T-ALL leukosialin was the disialylated hexasaccharide. The disialylated tetrasaccharide together with small amounts of the monosialylated pentasaccharide and the monosialylated trisaccharide are also present (FIG. 4B and 5B). These results are summarized in Table I, and indicate that leukosialin having high molecular weight contains more of the hexasaccharides than leukosialin with low molecular weight.

TABLE I

Structures and relative amounts of the O-linked oligosaccharides found on leukosialin from normal and leukemic T-lymphocytes. The numbers are expressed as % of the total O-linked oligosaccharides in a molar ratio.

| Leukosialin oligosaccharides | T-CLL | T-ALL | Thymocytes | Normal T-lymphocytes |
|---|---|---|---|---|
| Gal$\beta$1→3(NeuNAc$\alpha$2→6)GalNAcOH[a] | 35.0% | 27.6% | 26.0% | 30.6% |
| NeuNAc$\alpha$2→3Gal$\beta$1→3GalNAcOH | | | | |
| NeuNAc$\alpha$2→3Gal$\beta$1→3(NeuNAc$\alpha$2→6)GalNAcOH | 45.7% | 21.5% | 32.5% | 65.8% |
| Gal$\beta$1→3(NeuNAc$\alpha$2→3Gal$\beta$1→4 GlcNAc$\beta$1→6)GalNAcOH | 8.4% | 19.0% | 14.6% | 1.6% |
| NeuNAc$\alpha$2→3Gal$\beta$1→3(Gal$\beta$1→4 GlcNAc$\beta$1→6)GalNAcOH | | | | |
| NeuNAc$\alpha$2→3Gal$\beta$1→3(NeuNAc$\alpha$2→3 Gal$\beta$1→4GlcNAc$\beta$1→6)GalNAcOH | 10.9% | 32.0% | 26.8% | 2.0% |

[a]This oligosaccharide is minimumly present.

To confirm these results, cells were labeled by the alternative galactose oxidase/NaB[$^3$H]$_4$ procedure after sialidase treatment, and leukosialin was immunoprecipitated with anti-leukosialin antibodies. Immunoprecipitated protein was digested with Pronase (FIG. 1B, lanes 4 and 5), glycopeptides of high molecular weight were isolated by Sephadex G-50 gel filtration, and O-glycans were released from the glycopeptides by alkaline borohydride treatment as described above. The isolated released O-glycans were then subjected to Bio-Gel P-4 gel filtration and HPLC.

FIGS. 6A–6B show that Gal$\beta$1→3(Gal$\beta$1→4GlcNAc$\beta$1→6) GalNAcOH and Gal$\beta$1→3GalNAcOH were obtained in both chromatographic conditions but T-ALL leukosialin contains more of the asialo-tetrasaccharide than the asialodisaccharide, whereas the reverse is true for T-CLL leukosialin. The molar ratios of the tetrasaccharide to the disaccharide were found to be 21:79 for T-CLL leukosialin and 52:48 for T-ALL leukosialin. These ratios are consistent with the ratio obtained on sialylated saccharides (see Table 1), indicating that the results obtained by these two methods reflect the actual amounts of oligosaccharides.

EXAMPLE III

Immunoblotting of Leukosialin With Specific Antibodies

This example shows detection of high and low molecular weight leukosialin by immunoblot.

Results from chromatographic analysis indicated that leukosialin with different molecular weights could be visualized by immunological detection on Western blots. Cell lysates were separated by SDS-polyacrylamide gel electrophoresis and the proteins were electrophoretically blotted to nitrocellulose filters. These filters were then incubated with either rabbit anti-leukosialin antiserum or mouse T-305 monoclonal antibody.

Briefly, cells were lysed in the same lysing buffer used for radioactively labeled cells and the lysates were briefly centrifuged. The supernatants were boiled in sample buffer and subjected to SDS-polyacrylamide gel electrophoresis using 8% acrylamide gels. Proteins in the gel were transferred electrophoretically to a nitrocellulose filter in a Bio-Rad Trans Blot Cell. The efficiency of this transfer was checked by monitoring the transfer of prestained SDS-PAGE standards (Bio-Rad) to the nitrocellulose filter. The nitrocellulose was incubated with PBS containing 3% bovine serum albumin (BSA) for 2 hours at room temperature, and then reacted with rabbit anti-leukosialin antiserum or mouse monoclonal antibody T-305. The anti-leukosialin antiserum was diluted 1:1000 fold in Tris-buffered saline, TBS (10 mM Tris-HCl, pH 8.0 and 150 mM NaCl) containing 3% BSA and 0.05% NaN$_3$. After washing with TBS, the nitrocellulose was reacted with alkaline phosphatase-conjugated goat anti-rabbit immunoglobulins for 2 hours at room temperature. The nitrocellulose was washed with TBS and then incubated with reagents (5-Bromo-4-chloro-3-indolyl phosphate and nitroblue tetrazolium, both from Sigma, St. Louis, Mo.) for color development.

Mouse monoclonal antibody T-305 was prepared by immunizing mice with a T-ALL derived cell line, RPMI8402. This monoclonal antibody was shown to react strongly with T-lymphocytes in peripheral blood of patients with infectious mononucleosis, graft-VS-host disease after bone marrow transplantation, Acquired Immune Deficiency syndrome (AIDS) and acute leukemia. The T-305 antibody recognizes a carbohydrate dependent epitope on leukosialin expressed on activated T-cells, Fox, R. I., J. Immunol. 131:762 (1983), and Sportsman et al., J. Immunol. 135:158 (1985), both of which are incorporated herein by reference. The tissue-culture medium of monoclonal antibody T-305 was used at a protein concentration of 5 $\mu$g/ml. These filters were further incubated with alkaline phosphatase-conjugated goat anti-mouse immunoglobulins followed by the reagents for color development as described above.

As shown in FIGS. 7A–7B, the rabbit anti-leukosialin antiserum detects all leukosialins regardless of size (lanes 1–6 in FIG. 7A), while the T-305 monoclonal antibody detects only leukosialin with high molecular weight, in particular leukosialin from T-ALL and HSB-2 cells (lanes 7–12 in FIG. 7A). The apparent molecular weight of leukosialin recognized by T-305 is larger than that of the nonreactive form (for example, compare lane 4 and lane 10 in FIG. 7A), suggesting that T-305 recognizes the hexasaccharides attached to leukosialin. In contrast to T-ALL cells, T-CLL cells barely express any leukosialin that reacts with T-305 (lane 11 in FIG. 7A). When peripheral lymphocytes of a normal individual were analyzed, the T-305 monoclonal antibody detected a high molecular weight of leukosialin that was a minor component of the total leukosialin content (compare lane 2 and lane 8 of FIG. 7A). These results are consistent with the results obtained by structural analyses of oligosaccharides.

Leukosialin becomes a high molecular weight form when it contains more complex hexasaccharides, which in turn react with the T-305 monoclonal antibody. The rabbit anti-leukosialin atiserum, on the other hand, reacts with leukosialin regardless of glycosylation status because it reacts with the peptide moiety of leukosialin.

EXAMPLE IV

Comparison of Leukosialin from Leukemic Cells, Thymocytes and Normal T-lymphocytes This example demonstrates that T-lymphocytic leukemia cells re-express oligosaccharides which are present on immature cells.

To investigate whether the complex hexasaccharides present in leukemic cells can be regarded as re-expression of the saccharides on immature cells, leukosialin from thymocytes was examined. FIG. 1A (lane 9) shows leukosialin from thymocytes is heterogenous in molecular weight, with a major band slightly larger than leukosialin from normal T-lymphocytes. O-Glycans from thymocyte leukosialin were similarly prepared and analyzed by Bio-Gel P-4 gel filtration (FIG. 4D). The results show that thymocyte leukosialin contains a significant amount of the disialylated hexasaccharide (peak 1), in contrast to leukosialin in normal peripheral lymphocytes with almost exclusively the disialylated tetrasaccharide (Peak 2, FIG. 4C).

These results indicate that immature T-lymphocytes, isolated as thymocytes and leukemic cells share the property of expressing the complex hexasaccharides, that are barely detectable in the peripheral lymphocytes of normal individuals.

EXAMPLE V

Comparison of Glycosyltransferase Activities Between Normal and Leukemic Lymphocytes This example demonstrates that T-ALL cells exhibit significant amounts of $\beta 1 \rightarrow 6N$-acetylglucosaminyltransferase activity.

To understand the mechanisms underlying the differences in O-glycans attached to leukosialin, the activities of four glycosyltransferases were measured. Among them, $\beta 1 \rightarrow 6N$-acetylglucosaminyltransferase (core 2 GlcNAc transferase) is a key enzyme required to form the hexasaccharide NeuNAc$\alpha 2 \rightarrow 3$Gal$\beta 1 \rightarrow 4$GlcNAc$\beta 1 \rightarrow$(NeuNAc$\alpha 2 \rightarrow 3$Gal$\beta 1 \rightarrow$)GalNAc. $\alpha 2 \rightarrow 6$Sialyltransferase, on the other hand, adds a sialic acid residue at the same site where an N-acetylglucosamine residue is added by $\beta 1 \rightarrow 6N$-acetylglucosaminyltransferase.

The glycosyltransferases were assayed in total cell homogenates (5–10×10$^7$ cells) prepared by hypotonic lysis in 15 mM cacodylate buffer, pH 7.0, 2 mM phenylmethylsulfonyl fluoride, and 2 mM EDTA and by several passages through 26 gauge needles. The samples were assayed for protein concentration, diluted to 10 mg of protein/ml, and stored at −20° C. until use. All assays were carried out in duplicate with two enzyme concentrations, and controls without acceptors were used to correct for the degradation of the donor substrate and incorporation into endogenous acceptors. The protocol of glycosyltransferase assay was according to previous reports with slight modification.

Briefly, UDP-GlcNAc:Gal$\beta 1 \rightarrow 3$GalNAc $\beta 1 \rightarrow 6N$-acetylglucosaminyltransferase was assayed in a 25 μl total volume mixture containing 50 mM cacodylate buffer, pH 6.5, 0.1% Triton X-100, 1 mM UDP-[$^3$H]GlcNAC (25,000 cpm/nmol), 2 mM Gal$\beta 1 \rightarrow 3$GalNAc$\alpha$-O-p-nitrophenyl and 50 or 100 μg protein, Brockhausen, I., Biochemistry 24:1866 (1985), which is incorporated herein by reference. After incubation at 37° C. for 30 minutes or 1 hour, the reaction was stopped with 0.4 ml of 20 mM sodium tetraborate/1 mM EDTA (pH 9.1) and the mixture passed through a column (0.5×4 cm) of Dowex 1×8 (Cl−) equilibrated in water. The column was washed with 2.5 ml of water and the total eluate was used for counting.

The assay mixture for UDP-Gal:GlcNAc $\beta 1 \rightarrow 4$galactosyltransferase contained in a total volume of 25 μl: 50 mM cacodylate buffer, pH 7.4, 20 mM MnCl$_2$, 0.1% Triton X-100, 0.1% BSA, 0.1 mM UDP-[$^3$H]galactose (100,000 cpm/nmol), 10 mM GlcNAc and 50 or 100 μg protein, Barker, R., J. Biol. Chem. 247:7135 (1972), which is incorporated herein by reference. After incubation at 37° C. for 30 minutes or 1 hour, the reaction was stopped with 0.4 ml of ice-cold water. The products were analyzed as described above for $\beta 1 \rightarrow 6N$-acetylglucosaminyltransferase.

CMP-NeuNAc:GalNAc $\alpha 2 \rightarrow 6$sialyltransferase was assayed in a 25 μl total volume mixture containing 50 mM cacodylate buffer, pH 6.5, 1% Triton X-100, 0.1% BSA, 0.5 mM CMP-[$^{14}$C]NeuNAc (20,000 cpm/nmol), 100 μg asialo-bovine submaxillary mucin (BSM) and 50 or 100 μg protein. After incubation at 37° C. for 30 minutes or 1 hour, the reaction was stopped by placing the tube on ice. The reaction mixture was applied to a column (0.6×18 cm) of Sephadex G-50 equilibrated with 0.2 M NaCl, then 0.5 ml fractions were collected. The first three fractions were found to have negligible amount of radioactivity, and the sialylated product eluted in the following three fractions: CMP-[$^{14}$C]NeuNAc eluted in fractions 8–17. In order to make a specific substrate, asialo-BSM had been digested with O-glycanase (Genzyme, Boston, Mass.) to remove Gal$\beta 1 \rightarrow 3$GalNAc. The digested BSM should no longer be a substrate for Gal$\beta 1 \rightarrow 3$GalNAc $\alpha 2 \rightarrow 3$sialyltransferase as described.

CMP-NeuNAc:Gal$\beta 1 \rightarrow 3$GalNAc$\alpha 2 \rightarrow 3$ sialyltransferase was assayed in 25 μl of buffer containing 50 mM cacodylate buffer, pH 6.5, 1% Triton X100, 0.1% BSA, 6 μM CMP-[$^{14}$C]NeuNAc (300,000 cpm/nmol), 2 mM Gal$\beta 1 \rightarrow 3$GalNAc (Sigma) and 50 or 100 μg protein. After incubation at 37° C. for 30 minutes or 1 hour, the reaction was stopped with 1.0 ml f ice-cold 5 mM sodium phosphate buffer, pH 6.8. The reaction mixture was applied to a column (0.5×4 cm) of Dowex 1-X8 (phosphate form) prepared as described by Paulson, J. C., J. Biol. Chem. 252:2363 (1977), which is incorporated herein by reference. The column was washed with 3.0 ml of 5 mM sodium phosphate buffer, pH 6.8, and the total eluate was used for counting.

As shown in Table II, normal T-lymphocytes as well as K562 cells expressed a negligible amount of $\beta 1 \rightarrow 6N$-acetylglucosaminyltransferase. These results are consistent with the fact that normal T-lymphocytes and K562 cells express negligible amounts of the branched hexasaccharide NeuNAc$\alpha 2 \rightarrow 3$Gal$\beta 1 \rightarrow 4$GlcNAc$\beta 1 \rightarrow 6$-(NeuNAc$\alpha 2 \rightarrow 3$Gal$\beta 1 \rightarrow 3$)GalNAc.

In contrast, T-ALL cells contained a significant amount of $\beta 1 \rightarrow 6N$-acetylglucosaminyltransferase activity. To a lesser extent, T-CLL cells also express $\beta 1 \rightarrow 6N$-acetylglucosaminyltransferase, which is approximately half of $\beta 1 \rightarrow 6N$-acetylglucosaminyltransferase present in HSB-2 cells. These results correlate with the expression of the amounts of branched hexasaccharide, NeuNAcα2→3Galβ1→4GlcNAcβ1→6-(NeuNAc2→3Galβ1→3)GalNAc on T-ALL and on T-CLL and why T-CLL cells. The other three enzymatic activities measured remained constant compared to normal T-lymphocytes. These results indicate that the formation of the branched hexasaccharide is directly proportional to the activity of β1→6N-acetyl-glucosaminyltransferase.

TABLE II

| Glycosyltransferase Activities in Normal Resting T-Lymphocytes and Leukemic Cells | | | | | | |
|---|---|---|---|---|---|---|
| | T-CLL | T-ALL | Normal T lymphocytes nmol/h/mg protein | K-562 | HL-60 | HSB-2 |
| Galβ1→3GalNAc:β1→6GlcNAc transferase | 0.15 ± 0.01 | 1.10 ± 0.04 | 0.04 ± 0.01 | <0.02 | 0.54 ± 0.03 | 0.30 ± 0.02 |
| GalNAc:α2→6NeuNAc transferase | 0.57 ± 0.12 | 0.40 ± 0.10 | 0.47 ± 0.04 | 0.34 ± 0.03 | 0.33 ± 0.02 | 0.20 ± 0.01 |
| Galβ1→3GalNAc:α2→3NeuNAc transferase | 0.14± 0.01 | 0.17 ± 0.05 | 0.13 ± 0.01 | 0.20 ± 0.03 | 0.22 ± 0.09 | 0.12 ± 0.03 |
| GlcNAc:β1→4Gal transferase | 14.8 ± 3.1 | 13.0 ± 0.1 | 16.2 ± 1.6 | 16.6 ± 1.1 | 11.9 ± 1.3 | 14.1 ± 2.9 |
| β1→6GlcNAc transferase | 0.26 | 2.75 | 0.09 | <0.06 | 3.73 | 1.50 |
| α2→6NeuNAc transferase | | | | | | |

Glycosyltransferase activities were assayed as described in "Experimental Procedures." Enzyme activities are shown as the values of donor substrate incorported into exogenous acceptor (nmol/h/mg of protein). The mean and the standard errors of three preparations are given. The detection limit for these assays was approximately 0.02 nmol/h/mg of protein.

EXAMPLE VI

Characterization of Peripheral Blood Lymphocytes From WAS Patients by Immunofluorescence Analysis This example shows that unstimulated WAS T-lymphocytes react with the T305 monoclonal antibody but do not exhibit other activation antigens.

Blood samples from WAS patients or healthy volunteers were collected in EDTA (12.5 mM final conc.) and mononuclear cells were prepared by centrifugation over a Ficoll-Hypaque (Pharmacia) gradient. Monocytes were removed by adherence to plastic dishes in RPMI 1640 with 10% fetal calf serum (Gibco/BRL, Grand Island, N.Y.). The preparations usually contained more than 95% viable cells and between 80 and 85% CD3 positive cells. T-lymphocytes were activated by incubation of peripheral blood mononuclear cells in RPMI 1640 supplemented with 10% fetal calf serum, 50 ng/ml anti-CD3 (OKT-3, Ortho Diagnostics, Raritan, N.J.) and 50 U/ml interleukin-2 (Janssen Biochemicals, Beerse, Belgium) for six days with one change of medium on day 3. Immunofluorescence analysis was carried out on an Ortho Spectrum III cytofluorimeter set up for double fluorescence analysis. Forward angle light scatter was used to exclude dead cells. The results are presented as fluorescence histograms with the relative number of cells on a linear scale plotted vs. the relative fluorescence intensity on a logarithmic scale, both in arbitrary units.

Unstimulated WAS lymphocytes, unstimulated normal lymphocytes and in vitro activated normal lymphocytes were analyzed with antibodies to CD3, IL-2 receptor alpha chain (CD25) and a monoclonal antibody, T305 (FIGS. 8A-8I). Eighty percent of the cells from all three specimens were CD3+. In the unstimulated normal lymphocytes only 10% of the cells reacted with the T305 antibody whereas more than 50% of the unstimulated WAS lymphocytes were stained with the T305 antibody. T305 bound to almost 100% of in vitro activated normal T-lymphocytes incubated for 6 days with anti-CD3 and IL-2. Although the unstimulated WAS T-lymphocytes reacted with the T305 antibody, they were negative for the IL-2 receptor (FIG. 8E) and other activation antigens such as 4F2 and HLA-DR. Double labeling experiments with T305 and anti-CD3 antibodies documented that about 85% of the T305 positive WAS lymphocytes were CD3+.

EXAMPLE VII

Western Blot Analysis of Leukosialin from WAS Lymohocytes

This example shows that T-lymphocytes from WAS patients exhibit a high molecular weight form of leukosialin which is immunoreactive with the monoclonal antibody T305.

Peripheral blood lymphocytes from WAS patients were analyzed by immunoblotting as described in Example III using a specific anti-leukosialin antiserum. In all five patients (FIGS. 9a and 9c), the anti-leukosialin antiserum revealed a band at 135 kD with variable intensity. Two patients (FIG. 9A, lanes 3 and 5) revealed detectable bands only at 135 kD while two other patients (FIG. 9A, lanes 2 and 4) showed additional bands of equal intensity at 100 kD and 80 kD, respectively. The fifth patient (FIG. 9C, lane 1) had bands at 135 kD and at 120 kD. The peripheral blood lymphocytes of normal donors showed only a single band at 120 kD which corresponds to the molecular mass of leukosialin in normal resting T-lymphocytes. The proteins which are stained at 200 kD and at 70 kD are not related to leukosialin, Carlsson, S. R., J. Biol. Chem. 261:12787 (1986), which is incorporated herein by reference. To determine the molecular mass of leukosialin on normal T-lymphocytes activated in vivo, lymphocytes from the synovial fluid of a patient with rheumatoid arthritis were analyzed and revealed a broad leukosialin band from 120 to 135 kD (FIG. 9A, lane 6).

The murine monoclonal antibody T305 reacted with the 135 kD band of leukosialin of lymphocytes from WAS patients and of the synovial fluid lymphocytes from the patient with rheumatoid arthritis (FIG. 9B and C). The lower molecular mass forms of leukosialin at 120 kD was not recognized by T305.

EXAMPLE VIII

Immunoprecipitation of Leukosialin Labeled in its Carbohydrate Part

This example shows the immunoprecipitation of a single high molecular weight form of leukosialin from WAS T-lymphocytes.

Normal and WAS peripheral blood lymphocytes were labeled in their carbohydrate portions by galactose oxidase/sodium borohydride treatment as described in Example II. Immunoprecipitation of normal lymphocytes with rabbit anti-leukosialin antiserum gave a labeled band at 120 kD while the WAS lymphocytes gave a band of 135 kD (FIG. 10, lane 3). After removal of the sialic acid residues, the apparent molecular mass of leukosialin from the WAS patient shifted to about 170 kD (FIG. 10, lane 4) whereas normal asialo-leukosialin migrated at 150 kD (FIG. 10, lane 2). Following carbohydrate labeling, immunoprecipitation of leukosialin from WAS T-lymphocytes revealed only one band from both native and sialidase-treated lymphocytes indicating that the material of lower molecular mass present on Western blots of lysates from some WAS patients (FIGS. 9A-9C) not present in the patient tested or that these lower molecular mass forms of leukosialin do not contain sufficient amounts of carbohydrate to be detectable.

EXAMPLE IX

Carbohydrate Analysis of Leukosialin from WAS Lymohocytes

This example shows that the oligosaccharide structure found on WAS T-lymphocytes is that expressed on activated T-lymphocytes.

The labeled oligosaccharides released from cell surface-labeled WAS lymphocytes were analyzed by gel filtration on Bio-Gel P-4 and by HPLC on a Lichrosorb-NH$_2$ column as described in Example II. Irrespective of whether the labeling occurred through the sialic acid residues or after removal of the sialic acid through galactose or N-acetylgalactosamine, the oligosaccharides released by alkaline borohydride treatment from immunoprecipitated leukosialin from WAS lymphocytes displayed a different elution profile (FIGS. 11A-11F) than the oligosaccharides obtained from normal lymphocytes. The major oligosaccharide from native or sialidase-treated WAS leukosialin eluted in gel filtration earlier than the predominant oligosaccharide from normal CD 43 indicating a higher molecular mass for the patient's oligosaccharide. In the HPLC system, the sugars released from leukosialin of WAS lymphocytes eluted later than those from normal lymphocytes indicating again a more complex structure for the carbohydrates derived from WAS lymphocytes. In both analytical systems, the elution profile of saccharides from WAS leukosialin resembled closely the pattern of those obtained from activated normal T-lymphocytes.

The major structure released from native WAS leukosialin co-eluted from the gel filtration as well as from the HPLC column with the standard oligosaccharide NeuNAcα2→3Galβ1→3(NeuNAcα2→3Galβ1→4GlcNAcβ1→6)GalNAcOH. After removal of the sialic acid residues and labeling in the galactose moieties, the major oligosaccharide from WAS leukosialin eluted at the same position as Galβ1→3-(Galβ1→4GlcNAcβ1→6)GalNAcOH in both gel filtration and HPLC. The relative amounts of labeled oligosaccharides released from leukosialin from WAS as well as normal resting and activated lymphocytes are summarized in Table III.

TABLE III

| Relative amounts of oligosaccharides released from leukosialin | | | |
|---|---|---|---|
| Oligosaccharides | resting normal PBL [%] | WAS PBL [&] | activated normal PBL [%] |
| NeuNAcα2→3Galβ1→3(NeuNAcα2→3Galβ1→4GlcNAcβ1→6)GalNAcOH | 4.9 | 63.0 | 48.0 |
| NeuNAcα2→3Galβ1→3(NeuNAcα2→6)GalNAcOH | 69.0 | 18.3 | 19.0 |
| NeuNAcα2→3Galβ1→3(Galβ1→4GlcNAcβ1→6)GalNAcOH | 7.5 | 10.6 | 20.0 |
| Galβ1→3(NeuNAcα2→3Galβ1→4GlcNAcβ1→6)GalNAcOH Galβ1→3(NeuNAcα2→6)GalNAcOH NeuNAcα2→3Galβ1→3GalNAcOH | 18.5 | 8.0 | 13.0 |

EXAMPLE X

Biosynthesis of O-linked Carbohydrates in WAS Lymphocytes

In order to study the biosynthetic mechanisms underlying the change of O-glycan structure in WAS T-lymphocytes, microsomal preparations of normal and WAS lymphocytes were analyzed for the enzymatic activities of six glycosyltransferases. These enzymes are known to be involved in the biosynthesis of O-linked carbohydrate structures and specific assay protocols are described in Example V for four of the six transferases. The remaining two transferases were assayed as described in Piller et al. supra. Briefly, UDP-GalNAc:-protein α-N-acetylgalactosaminyltransferase was assayed using 200 μg of apo-BSM (apo-Bovine Submaxillary Mucin) while UDP-Gal:GalNAcβ1→3galactosyltransferase used 200 mM GalNAc as acceptor substrates. Enzymatic activities were calculated from the radioactivity transferred from [$^{14}$C]-labeled sugar nucleotide donor substrates to specific well defined acceptor substrates. The transfer rates were corrected for non-specific degradation and for the transfer to endogenous substrates in the enzyme preparations by subtracting the values obtained with control incubations from which the acceptor substrates were omitted. The mean transfer rates of two protein concentrations are shown in Table IV.

Five of the six enzymes displayed comparable activities in resting normal and WAS lymphocytes. In contrast, the β1→6GlcNAc transferase was only barely detectable (0.05 nmol/h mg protein) in normal lymphocytes whereas its activity was comparable to that of other glycosyltransferases (0.4 nmol/h mg protein) in WAS lymphocytes. The labeled product of the β1→6 GlcNAc transferase reaction was characterized by HPLC analysis on a reversed phase column. The elution time of the product (22 minutes) corresponded to that of the standard compound Galβ1→3(GlcNAcβ1→6)GalNAcα1→O-benzyl which is the structure synthesized by the β1→6GlcNAc transferase in the assay system used, Brockhausen, I., Eur. J. Biochem. 157:463 (1986), which is incorporated herein by reference.

TABLE IV

| Glycosyltransferase Activities | | |
|---|---|---|
| Enzymes | Normal lymphocytes [nmol/h.mg protein] | WAS lymphocytes [nmol/h.mg protein] |
| Polypeptide: αGalNAc transferase | 0.33 | 0.2 |

TABLE IV-continued

| | Glycosyltransferase Activities | |
|---|---|---|
| Enzymes | Normal lymphocytes [nmol/h.mg protein] | WAS |
| GalNAC: $\beta1\rightarrow3$ Gal transferase | 0.17 | 0.26 |
| Gal$\beta1\rightarrow$3GalNAc: $\beta1\rightarrow6$ GlcNAc transferase | 0.05 | 0.4 |
| GlcNAc: $\beta1\rightarrow4$ Gal transferase | 2.38 | 1.49 |
| GalNAC: $\alpha2\rightarrow6$ NeuNAc transferase | 3.08 | 2.56 |
| Gal$\beta1\rightarrow$3GalNAc: $\alpha2\rightarrow3$ NeuNAc transferase | 0.17 | 0.2 |

Glycosyltransferase activities were assayed in duplicates at two different protein concentrations. Incubations were carried out at 37° C. for 30 minutes.

although the invention has been described with reference to the presently-preferred embodiment, it should be understood that various modifications can be made by those skilled in the art without departing from the invention. Accordingly, the invention is limited only by the following claims.

We claim:

1. A method of detecting T-cell dysfunctions, comprising detecting an increase in the level of core 2 GlcNAc transferase regulating synthesis of the hexasaccharide NeuNAc$\alpha2\rightarrow$3Gal$\beta1\rightarrow$3(NeuNAc$\alpha2\rightarrow$3Gal$\beta1\rightarrow$4GlcNAc$\beta1\rightarrow$6)GalNAc on leukosialin of T-cells from a subject suspected of having a T-cell dysfunction compared to resting T-cells from a normal individual.

2. The method of claim 1, wherein said T-cell dysfunction is acute T-lymphocytic leukemia.

3. The method of claim 1, wherein said T-cell dysfunction is chronic T-lymphocytic leukemia.

4. The method of claim 1, wherein said T-cell dysfunction is Wiskott-Aldrich Syndrome.

5. The method of claim 1, wherein said increase in level comprises an increased amount of core 2 GlcNAc transferase.

6. The method of claim 1, wherein said increase in level comprises an increased activity of core 2 GlcNAc transferase.

7. The method of claim 5, wherein said detecting comprises binding the core 2 GlcNAc transferase with a ligand specific thereto and determining the amount of binding.

8. The method of claim 7, wherein said ligand is an antibody.

9. The method of claim 7, wherein said ligand is a substrate analogue.

10. A method of detecting T-cell dysfunctions comprising detecting an increase in the level of leukosialin having the hexasaccharide NeuNAc$\alpha2\rightarrow$3Gal$\beta1\rightarrow$3-(NeuNAc$\alpha2\rightarrow$3Gal$\beta1\rightarrow$4GlcNAc$\beta1\rightarrow$6)GalNAc on T-cells from a subject suspected of having a T-cell dysfunction compared to resting T-cells from a normal individual.

11. The method of claim 10, wherein said T-cell dysfunction is acute T-lymphocytic leukemia.

12. The method of claim 10, wherein said T-cell dysfunction is chronic T-lymphocytic leukemia.

13. The method of claim 10, wherein said increase in level comprises an increased amount of said hexasaccharide.

14. The method of claim 13, wherein said detecting comprises binding the hexasaccharide with a ligand specific thereto and determining the amount of binding.

15. The method of claim 14, wherein said ligand is an antibody.

* * * * *

UNITED STATES PATENT AND TRADEMARK OFFICE
CERTIFICATE OF CORRECTION

PATENT NO. : 5,320,943

DATED : June 14, 1994

INVENTOR(S) : Minoru Fukuda

Page 1 of 2

It is certified that error appears in the above-indentified patent and that said Letters Patent is hereby corrected as shown below:

Line 15 of the abstract, please delete ")GlcNAc" and insert therefor --)GalNAc--.

Column 3, line 9, please delete "6)GlcNAc" and insert therefor --6)GalNAc--.

Column 3, line 62, please delete "6)GalNaCOH," and insert therefor --6)GalNAcOH,--.

Column 5, line 18, please insert --(11C, 11F)-- after "IL-2" and before "are".

Column 8, lines 1-2, please delete "core GlcNAc-T" and insert therefor --core 2 GlcNAc-T--.

Column 11, Table I, the first line of oligosaccharides, please delete "GalβB1" and insert therefor --Galβ1--.

Column 13, line 46, please delete "3Galβ1→)GalNAc" and insert therefor --3Galβ1→3)GalNAc--.

Column 14, line 47, please delete "ml f ice-cold" and insert therefor --ml of ice-cold--.

Column 15, line 3, please delete "and why T-CLL cells."

UNITED STATES PATENT AND TRADEMARK OFFICE
CERTIFICATE OF CORRECTION

PATENT NO. : 5,320,943
DATED : June 14, 1994
INVENTOR(S) : Minoru Fukuda

It is certified that error appears in the above-indentified patent and that said Letters Patent is hereby corrected as shown below:

Column 19, line 16, please delete "although" and insert therefor --Although--.

Signed and Sealed this

Sixth Day of December, 1994

Attest:

BRUCE LEHMAN

Attesting Officer

Commissioner of Patents and Trademarks